US011883739B2

(12) United States Patent
Cooper et al.

(10) Patent No.: US 11,883,739 B2
(45) Date of Patent: Jan. 30, 2024

(54) REPLACEABLE LIQUID SCENT CARTRIDGE

(71) Applicant: OVR Tech, LLC, Burlington, VT (US)

(72) Inventors: Erik Cooper, Burlington, VT (US); Aaron Wisniewski, Burlington, VT (US); Matthew Flego, Burlington, VT (US); Samuel Wisniewski, Burlington, VT (US)

(73) Assignee: OVR Tech, LLC, Burlington, VT (US)

( * ) Notice: Subject to any disclaimer, the term of this patent is extended or adjusted under 35 U.S.C. 154(b) by 0 days.

(21) Appl. No.: 17/031,718

(22) Filed: Sep. 24, 2020

(65) Prior Publication Data

US 2021/0008446 A1 Jan. 14, 2021

Related U.S. Application Data

(63) Continuation-in-part of application No. 16/871,447, filed on May 11, 2020, now Pat. No. 11,351,449,
(Continued)

(51) Int. Cl.
*A63F 13/28* (2014.01)
*A63F 13/25* (2014.01)
(Continued)

(52) U.S. Cl.
CPC .............. *A63F 13/25* (2014.09); *A61L 9/122* (2013.01); *A61L 9/125* (2013.01); *A61L 9/14* (2013.01);
(Continued)

(58) Field of Classification Search
CPC .......... A63F 13/25; A63F 13/26; A63F 13/28; A63F 13/50; A63F 13/53; A63F 13/90;
(Continued)

(56) References Cited

U.S. PATENT DOCUMENTS

| 4,952,024 A | 8/1990 | Gale |
| 5,318,503 A | 6/1994 | Lord |

(Continued)

FOREIGN PATENT DOCUMENTS

| CA | 2814977 A1 | 5/2012 |
| CN | 102076387 A | 5/2011 |

(Continued)

OTHER PUBLICATIONS

International Search Report and Written Opinion dated Jan. 14, 2020 in connection with International Application No. PCT/US2019/057023.

(Continued)

*Primary Examiner* — Omkar A Deodhar
(74) *Attorney, Agent, or Firm* — Wolf, Greenfield & Sacks, P.C.

(57) ABSTRACT

A convenient system with replacement hardware is provided for rendering scents within a computing environment. In some implementations, a scent cartridge unit is provided that is replaceable within a scent-rendering hardware unit that is computer-controlled to render one or more scents to be experienced by a user. The scent-rendering hardware unit includes one or more aerosol generators that are adapted to release individual scents. In some implementations, more than one scent may be released at the same time, rendering a complex scent. In some implementations, base scent material may be provided within multiple aerosol generators within an array, and the base scent material may be released in predetermined amounts, durations, and intensities depending on the desired scent. The array may be electronically driven by signals provided by driver circuitry.

15 Claims, 26 Drawing Sheets

Related U.S. Application Data which is a continuation of application No. 16/219,028, filed on Dec. 13, 2018, now Pat. No. 10,688,389.

(60) Provisional application No. 62/905,974, filed on Sep. 25, 2019, provisional application No. 62/598,357, filed on Dec. 13, 2017.

(51) Int. Cl.
 *A61L 9/12* (2006.01)
 *G06F 3/01* (2006.01)
 *A63F 13/52* (2014.01)
 *A61L 9/14* (2006.01)

(52) U.S. Cl.
 CPC .............. *A63F 13/52* (2014.09); *G06F 3/01* (2013.01); *A61L 2209/111* (2013.01); *A61L 2209/132* (2013.01); *A61L 2209/133* (2013.01); *A63F 2250/021* (2013.01); *A63F 2300/308* (2013.01)

(58) Field of Classification Search
 CPC ............ A63F 2250/021; A63F 2250/30; A63F 2300/8082; A61L 9/125; G06F 3/011
 See application file for complete search history.

(56) References Cited

U.S. PATENT DOCUMENTS

| | | |
|---|---|---|
| 5,591,409 A | 1/1997 | Watkins |
| 5,610,674 A | 3/1997 | Martin |
| 5,898,475 A | 4/1999 | Martin |
| 6,231,032 B1 | 5/2001 | Ivey, Jr. |
| 6,296,196 B1 | 10/2001 | Denen et al. |
| 6,371,451 B1 | 4/2002 | Choi |
| 6,713,024 B1 | 3/2004 | Arnell et al. |
| 6,737,025 B2 | 5/2004 | Boyd et al. |
| 7,154,579 B2 | 12/2006 | Selander et al. |
| 7,395,507 B2 | 7/2008 | Robarts et al. |
| 7,584,903 B2 | 9/2009 | Koerner et al. |
| 7,651,077 B1 | 1/2010 | Rosener et al. |
| 7,913,933 B2 | 3/2011 | Van Roemburg |
| 8,012,023 B2 | 9/2011 | Gates, III et al. |
| 8,074,640 B2 | 12/2011 | Davies et al. |
| 8,341,022 B2 | 12/2012 | Edwards |
| 8,706,518 B2 | 4/2014 | Hyde et al. |
| 8,727,234 B2 | 5/2014 | Haran |
| 8,821,802 B2 | 9/2014 | Haran |
| 8,881,999 B2 | 11/2014 | Blaylock et al. |
| 9,283,296 B2 | 3/2016 | Haran et al. |
| 9,289,530 B2 | 3/2016 | Haran et al. |
| 9,446,162 B2 | 9/2016 | Chandler et al. |
| 9,586,228 B2 | 3/2017 | Roemburg et al. |
| 9,648,907 B2 | 5/2017 | Kobal et al. |
| 9,652,037 B2 | 5/2017 | Rubin et al. |
| 9,728,006 B2 | 8/2017 | Varga |
| 9,746,912 B2 | 8/2017 | Meijer et al. |
| 9,755,848 B2 | 9/2017 | Cieszkowski, III et al. |
| 9,811,854 B2 | 11/2017 | Lucido |
| 9,823,473 B2 | 11/2017 | Kobayashi |
| 9,872,968 B2 | 1/2018 | de Zambottti et al. |
| 9,904,358 B2 | 2/2018 | Rubin et al. |
| 9,907,876 B2 | 3/2018 | Jin et al. |
| 10,688,389 B2 | 6/2020 | Flego et al. |
| 11,013,264 B2 | 5/2021 | Sanchez et al. |
| 11,351,449 B2 | 6/2022 | Flego et al. |
| 11,351,450 B2 | 6/2022 | Flego et al. |
| 11,577,268 B2 | 2/2023 | Flego et al. |
| 2002/0129813 A1 | 9/2002 | Litherland et al. |
| 2007/0258849 A1 | 11/2007 | Kent |
| 2008/0092912 A1 | 4/2008 | Robinson et al. |
| 2010/0019057 A1 | 1/2010 | Duru et al. |
| 2011/0045050 A1 | 2/2011 | Elbayoumi et al. |
| 2011/0148607 A1 | 6/2011 | Zeleny |
| 2014/0374503 A1 | 12/2014 | Yoshimura et al. |
| 2015/0038869 A1 | 2/2015 | Simon et al. |
| 2016/0279435 A1 | 9/2016 | Hyde et al. |
| 2016/0296367 A1 | 10/2016 | Ivri |
| 2016/0363280 A1 | 12/2016 | Angelotti |
| 2017/0065000 A1 | 3/2017 | Sears et al. |
| 2017/0112666 A1 | 4/2017 | Fateh |
| 2017/0224938 A1 | 8/2017 | Power et al. |
| 2017/0274279 A1 | 9/2017 | Fateh |
| 2018/0071425 A1* | 3/2018 | Jin .......................... A61L 9/125 |
| 2018/0286351 A1 | 10/2018 | Fateh |
| 2019/0176034 A1 | 6/2019 | Flego et al. |
| 2020/0122182 A1 | 4/2020 | Flego et al. |
| 2020/0330860 A1 | 10/2020 | Flego et al. |
| 2021/0001214 A1 | 1/2021 | Wisniewski et al. |
| 2021/0121835 A1 | 4/2021 | Wisniewski et al. |
| 2023/0089379 A1 | 3/2023 | Flego et al. |

FOREIGN PATENT DOCUMENTS

| | | |
|---|---|---|
| CN | 106406548 A | 2/2017 |
| EP | 2 119 465 A1 | 11/2009 |
| EP | 1 598 084 A1 | 11/2015 |
| JP | 2001-129069 A | 5/2001 |
| JP | 2005-326907 A | 11/2005 |
| JP | 31-53624 U | 9/2009 |
| JP | 2014-092673 A | 5/2014 |
| JP | 2018-516719 A | 6/2018 |
| WO | WO 92/05229 A1 | 4/1992 |
| WO | WO 2009/067734 A1 | 6/2009 |
| WO | WO 2014/144690 A2 | 9/2014 |
| WO | WO 2015/143444 A1 | 9/2015 |
| WO | WO 2016/164917 A1 | 10/2016 |
| WO | WO 2016/179167 A1 | 11/2016 |
| WO | WO 2019/035786 A2 | 2/2019 |
| WO | WO 2019/118738 A1 | 6/2019 |

OTHER PUBLICATIONS

International Search Report and Written Opinion dated Apr. 5, 2019 in connection with International Application No. PCT/US2018/065476.
International Preliminary Report on Patentability dated Jun. 25, 2020 in connection with International Application No. PCT/US2018/065476.
International Search Report and Written Opinion dated Dec. 22, 2020 in connection with International Application No. PCT/US2020/052592.
International Search Report and Written Opinion dated Dec. 17, 2020 in connection with International Application No. PCT/US2020/052543.
International Search Report and Written Opinion dated Dec. 23, 2020 in connection with International Application No. PCT/US2020/052548.
International Preliminary Report on Patentability dated Apr. 29, 2021 in connection with International Application No. PCT/US2019/057023.
Ischer et al., How incorporation of scents could enhance immersive virtual experiences. Frontiers in Psychology. Jul. 17, 2014; 5:1-11.
EP 18887380.6, Oct. 26, 2021, Extended European Search Report.
Extended European Search Report dated Oct. 26, 2021 in connection with European Application No. 18887380.6.
Australian Examination Report dated Oct. 11, 2022, in connection with Australian Application No. AU 2018383640.
Japanese Office Action dated Oct. 17, 2022, in connection with Japanese Application No. JP 2020-551779.
U.S. Appl. No. 18/154,320, filed Jan. 13, 2023, Flego et al..
JP 2020-551779, Jun. 26, 2023, Japanese Decision of Rejection.
Decision of Rejection dated Jun. 26, 2023, in connection with Japanese Application No. 2020-551779.

* cited by examiner

| Proximity | Activity | Duration |
|---|---|---|
| Ambient
Burst
Specific | Passive
Active
Invisible
Predictive
Causal | Burst
Sustained
Undulating
Intervals |

FIG. 6

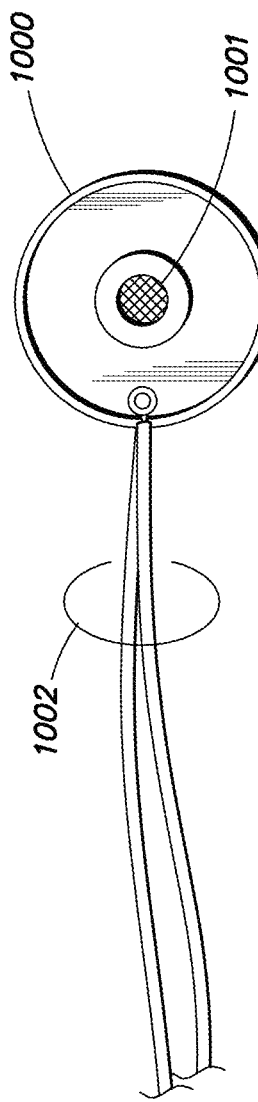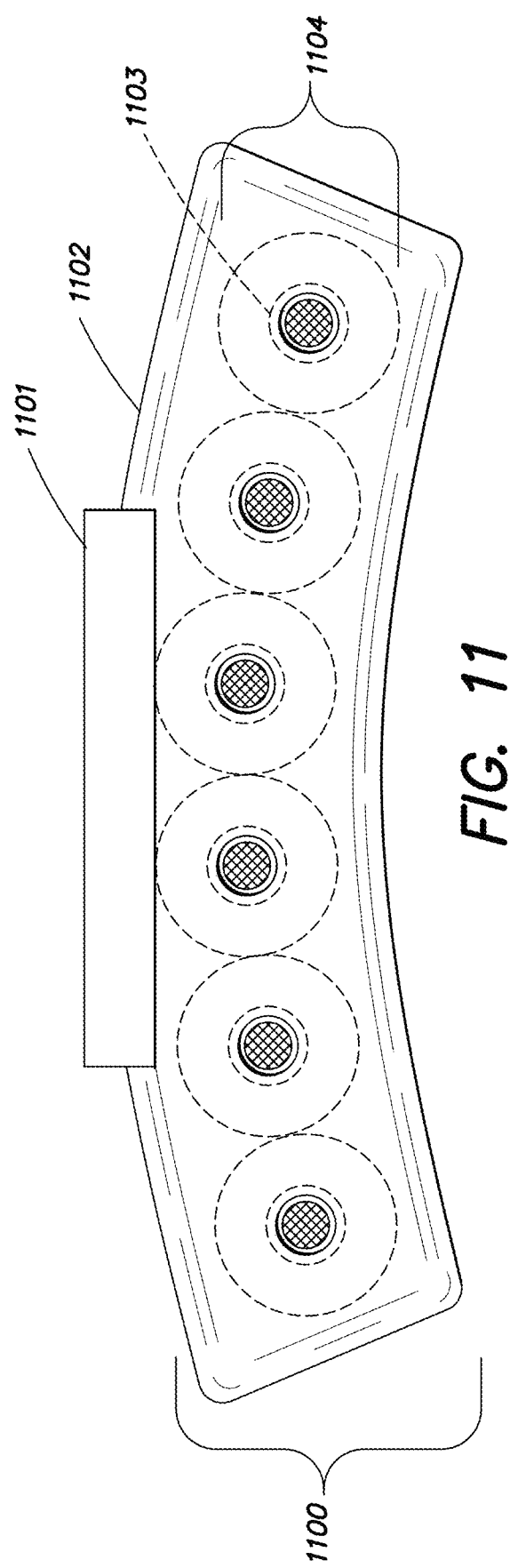

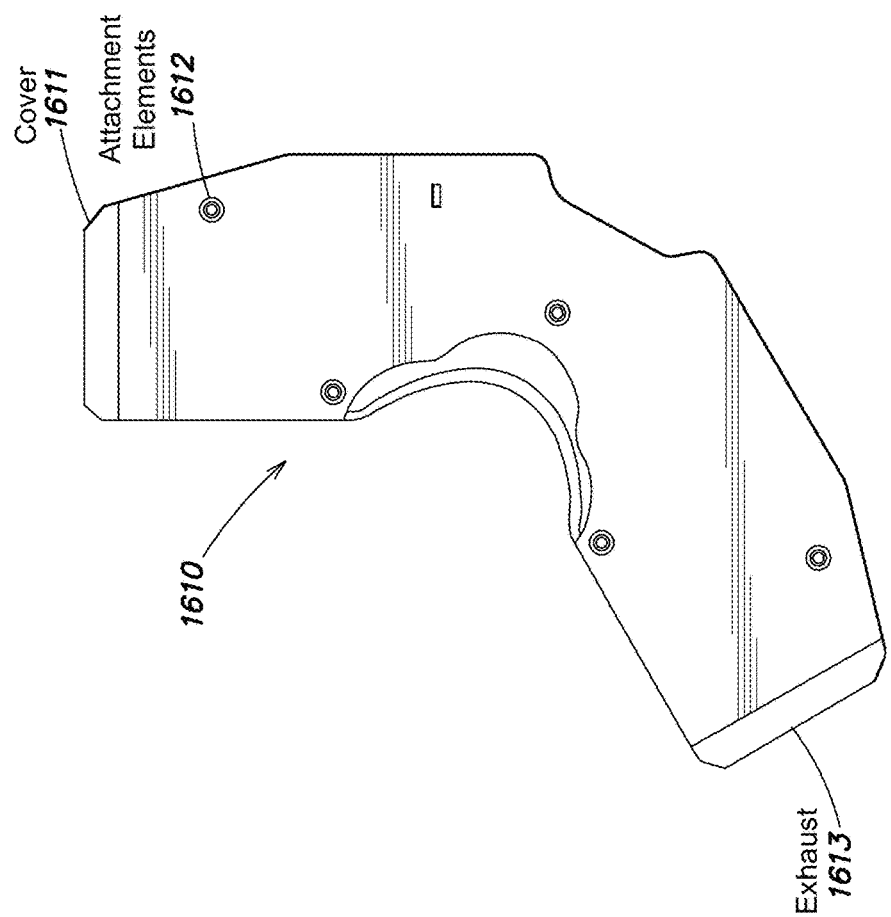
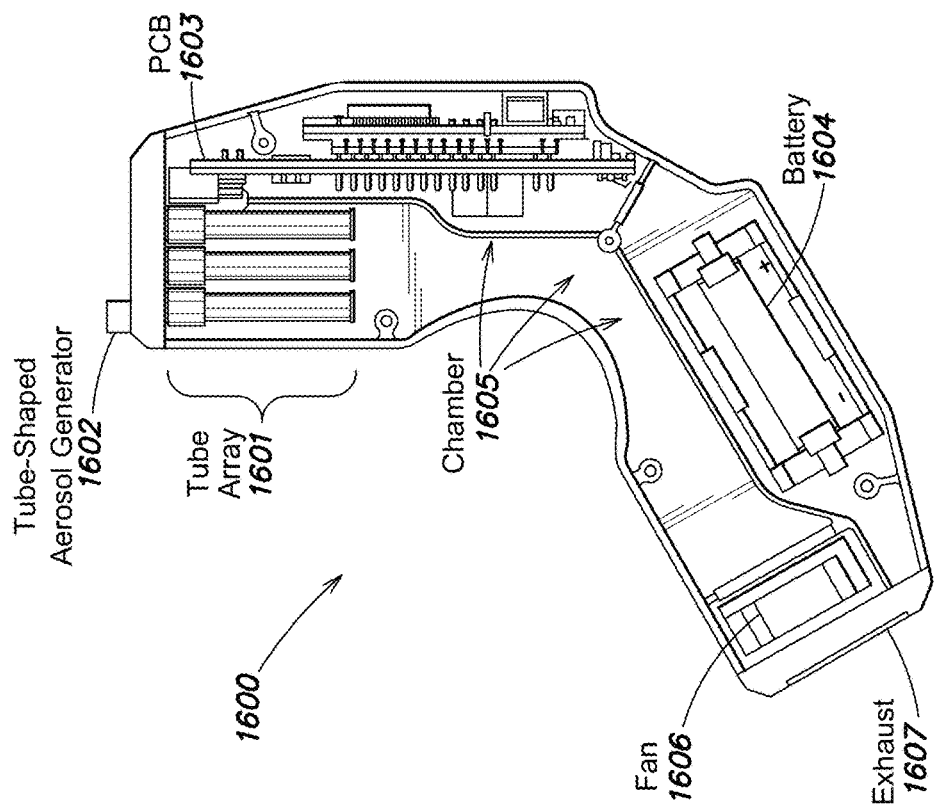
FIG. 16B
FIG. 16A

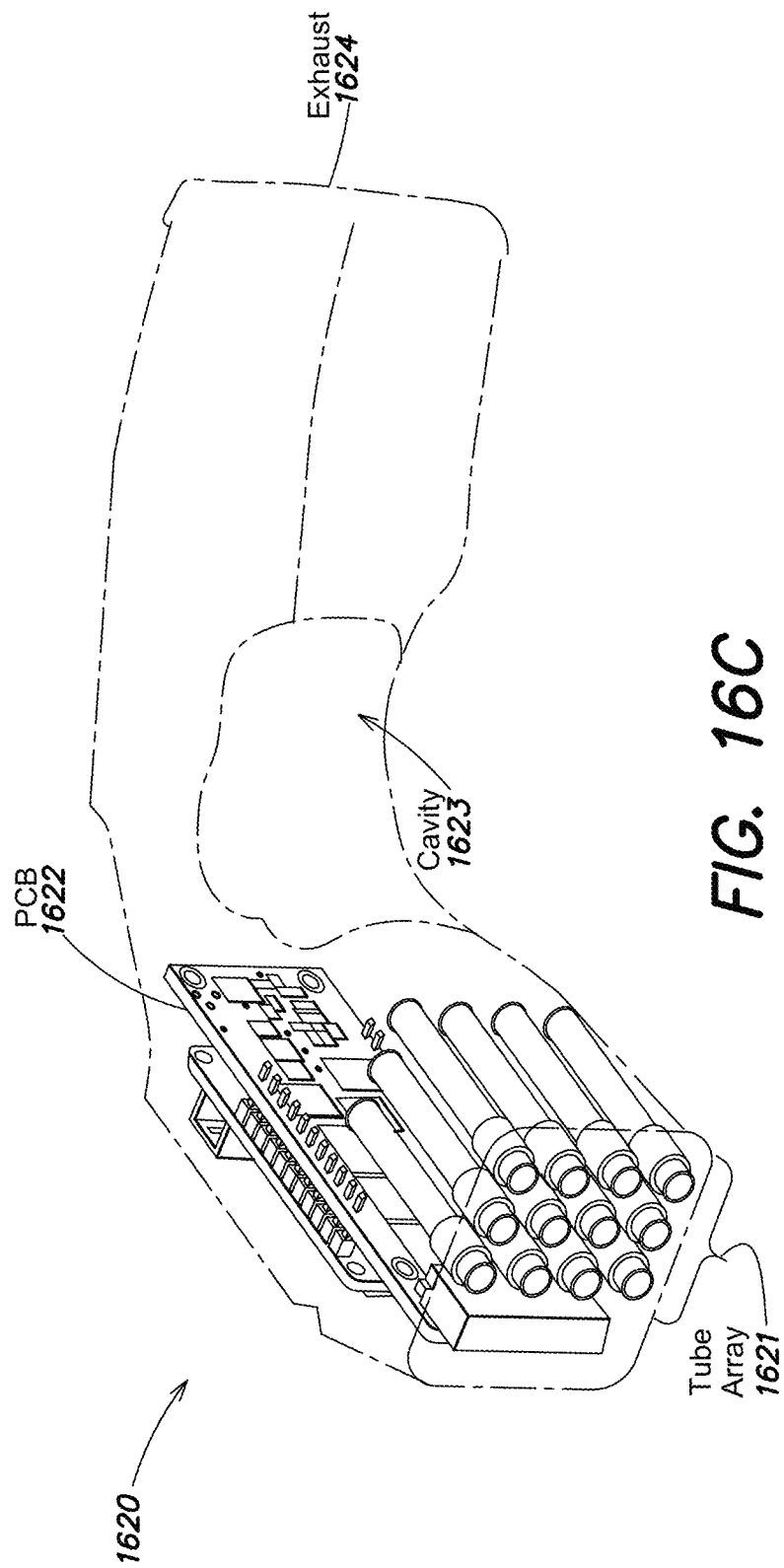

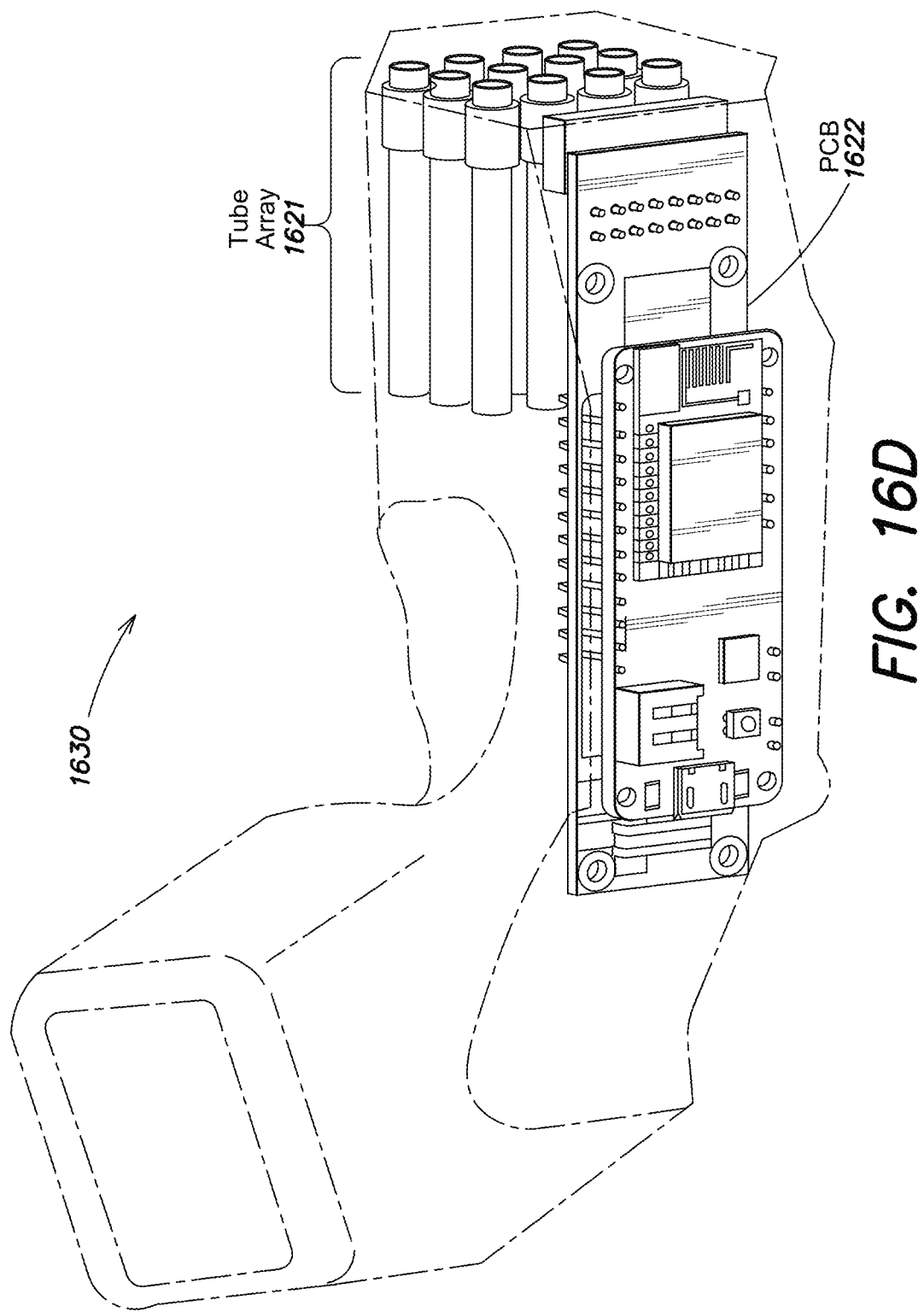

Cartridge Assembly *900*

PCB Board Assembly *918*

*919* Aerosol Generators

FIG. 19D

REPLACEABLE LIQUID SCENT CARTRIDGE

RELATED APPLICATIONS

This application is a Continuation-in-part of U.S. application Ser. No. 16/871,447, filed May 11, 2020, entitled "SYSTEM AND METHOD FOR GENERATING OLFACTORY STIMULI", which is a Continuation of U.S. application Ser. No. 16/219,028, filed Dec. 13, 2018, entitled "SYSTEM AND METHOD FOR GENERATING OLFACTORY STIMULI", which is a Non-Provisional of Provisional (35 USC 119(e)) of U.S. Application Ser. No. 62/598,357, filed Dec. 13, 2017, entitled "SYSTEM AND METHOD FOR GENERATING OLFACTORY STIMULI". This application is a Non-Provisional of Provisional (35 USC 119(e)) of U.S. Application Ser. No. 62/905,974, filed Sep. 25, 2019, entitled "REPLACEABLE LIQUID SCENT CARTRIDGE". The entire contents of these applications are incorporated herein by reference in their entirety.

SUMMARY

There are systems and devices that are capable of rendering scent stimuli within a computing environment, however, it is appreciated that widespread adoption of such systems have not occurred. It is appreciated that such systems would be more widely implemented if they were provided in a form factor that they could be used in traditional computing environments (e.g., with other AR/VR equipment). Some of the drawbacks of such systems includes that they are highly specialized and require the replacement of scented materials that makes their use inconvenient in certain settings.

In some embodiments as described herein, a convenient system with replacement hardware is provided for rendering scents within a computing environment. In some implementations, a scent cartridge unit is provided that is replaceable within a scent-rendering hardware unit that is computer-controlled to render one or more scents to be experienced by a user. The scent-rendering hardware unit includes one or more aerosol generators that are adapted to release individual scents. In some embodiments, more than one scent may be released at the same time, rendering a complex scent. In some implementations, base scent material may be provided within multiple aerosol generators within an array, and the base scent material may be released in predetermined amounts, durations, and intensities depending on the desired scent. The array may be electronically driven by signals provided by driver circuitry.

As discussed, the replaceable scent cartridge may interface with a scent-rendering hardware unit. The scent-rendering hardware unit may include multiple aerosol generator elements positioned in an array. In some embodiments, the scent-rendering hardware unit may include the aerosol generator units and associated circuitry along with a controller that is adapted to receive signals from one or more other systems (e.g., a gaming system, AR/VR system, etc.) to render scent to a user. In some embodiments, the replaceable scent cartridge may include individual scent media (e.g., liquids) located within small cavities within the cartridge. In various implementations, the replaceable cartridge may "plug" into the scent-rendering hardware unit which includes the aerosol generator units which atomizes the various scent media. In some embodiments, the scent-rendering hardware unit may include any necessary driver circuitry that drives the aerosol generator units.

In at least some example implementations, the cartridge unit contains a plurality of individual liquid scents (e.g., 9, 12, 24, 32, 36, etc.) in small cavities of some volume (e.g., a sub-milliliter volume) that allows a user to interchange the cartridge which plugs into the back of the scent-rendering hardware unit. Each volume of liquid then has a "straw" or cylindrical opening containing a wick or other wick-like element that leads from the fluid within the cavity and out a proximal end of the straw to meet a corresponding aerosol generator. In some embodiments, the aerosol generator includes an atomizer plate having holes through which the scent media is released. In some configurations, the wick for each individual scent extends into a corresponding aerosol generator, and the wick supplies scented liquid to the corresponding aerosol generator. In some configurations, the wick extends into the aerosol generator and contacts a back of the atomizer plate through which scent is released. In some implementations, tiny amounts of scented liquid are transferred from the cavities(s) to the respective atomizer plate(s) through capillary action of the respective wick(s). As an alternative or in addition to wick elements, the system may use one or more other component elements to provide liquid movement. For example, the system may use one or more microfluidics elements (e.g., micropumps, microvalves, capillary flow modifying elements, etc.) to transport, mix, separate, or otherwise process the scented liquids(s).

In some embodiments, the aerosol generator is a round, rectangular, or other shaped tube that vibrates responsive to a control signal, and forces scented liquid through the atomizer plate. In some implementations, the aerosol generator includes a piezoelectric element that vibrates at some frequency when activated. In some configurations, the wicks within the tubes do not contact the tube walls, and maintain a minimal gap on all sides to not impede vibrations of the piezoelectric element. Further, in some designs, the replaceable scent cartridge is coupled to the scent-rendering hardware unit using an attaching mechanism that forms a seal between the cartridge and the unit. In some implementations, a magnetic coupling attaches the cartridge to the unit, forming a seal between the cartridge and the unit.

Example Systems

In some embodiments described above, processes are provided for atomizing liquids such as those that may be vaporized by one or more scent delivery systems. For example, such scented liquids may be vaporized by one or more systems shown and discussed below which show various systems, methods and elements used to vaporize scented liquids in one or more applications.

Historically, there have been many attempts at providing scents in various environments, such as theaters, computer environments, among other situations and locations. However, many of these technologies failed to reach widespread adoption. Also, some attempts have been made to extend scents technology to virtual reality environments, however, it is appreciated that there is no common device available that is capable of rendering scents in such environments. According to some embodiments, a device is provided that is capable of rendering scent stimuli within an augmented and/or virtual reality environment, or any other type of computer-based application.

Such a device, according to some embodiments, may be provided as a companion device or may be fully embedded in an Extended Reality (XR), Virtual Reality (VR) or Altered Reality (AR) headset system (e.g., the well-known HTC Vive, Oculus Rift, Microsoft HoloLens, HTC's Gear VR among other devices and/or systems). The device, may, in some embodiments include a controller (or other type of processor) that is capable of communicating with a game (or content delivery) engine, operating system (e.g., Windows mixed reality, Google daydream) or other type of content delivery processor that produces XR (e.g., AR and/or VR content). In some embodiments, content can be created in a number of environments such as Unity, Unreal, Adobe, OpenXR, among others.

In some embodiments, the device, sometimes referred to herein as an OVR (olfactory virtual reality) device or system that provides olfactory stimuli, may include an aerosol generator or AG device for producing vaporized media to render scents. The AG device may include, for example, a piezoelectric vibration device that is used to produce scents corresponding to actions performed in an XR environment (e.g., VR or AR, or other type of environment). That is, in some implementations, a user interacts with one or more game elements within a game program being executed by the game engine, and responsive to the interaction, the game engine may communicate a series of commands that cause a piezoelectric device of the OVR device to generate scents to be experienced by the user. According to some embodiments, the game engine is coupled to the OVR device via one or more communication channels such as a wireless interface (e.g., Bluetooth, WiFi, etc.). The game engine (or other type of content producer) may communicate with the OVR device using a stream of serial data, which when received by the OVR device, may be translated to scent commands that operate one or more piezoelectric elements of the OVR device.

In some embodiments, the OVR device further includes one or more detachable elements (e.g., a vessel or other element type) that each contain a scent module. The detachable scent modules may, in some embodiments, include one or more scents that can be controlled by the game engine. There could be any number of small scent modules, each associated with a separate piezoelectric element that can be addressed and used to render a scent to the user. The scent modules may be constructed using an element that contains one or more scents, which can be in the form of liquid, gel or solid scent media.

In some embodiments, the microcontroller or other processor type controls an amplitude (and/or vibrational frequency) of a piezoelectric device which in turn controls airflow and scented media output that interacts with a corresponding detachable scent module. Other types of aerosol generating elements may be used in some embodiments. The volume of scent delivered to the user's olfactory organs are controlled more accurately using such a control. Also, in some embodiments, a larger range of rendered scent strengths may be produced as a result.

In some embodiments, there may be one or more stages of piezo elements used to render scent information. As discussed further below, some elements may be used to provide fine control of the outputs of specific scents, while other elements may be used to perform primarily airflow movement, alone or in addition to fan elements or other air moving devices. In some embodiments, the piezo elements may or may not have separate vessels that contain the scent media. In some instances, the piezo elements may come preloaded with scent media. Some types of piezo elements may provide a replaceable form of scent media, such as a wick, insert or other media-containing element. In some embodiments, the piezo driven device vibrates liquid through a fine mesh to an output an aerosol or other atomized output to the user's nose.

The piezo driven aerosol generator (AG) may take many forms, such as devices using vibrating mesh technology (VMT). For example, a ring-shaped piezo device formed around a plate with aperture holes having specified sizes may be used to vibrate a liquid into a fine mist that is dispersed in the air surrounding a user's nose. Such plates may be, in some embodiments, flat or formed (domed). In some embodiments and application types, the size of the holes may be less than 10 microns.

Other piezo-type devices may be used, such as tubes of various shapes and sizes that have a piezo element surface attached to a tube surface, and which is arranged to vibrate and force the liquid into a mist through an aperture plate having holes. It should be appreciated that other arrangements and types of piezo elements may be used. For example, rectangular tubes may be used with piezo elements attached to the sides. It should be appreciated that different types and shapes or piezo elements may be used. For instance, one or more of the elements described in U.S. patent application Ser. No. 16/657,313, entitled "DEVICE FOR ATOMIZING FLUID" filed Oct. 18, 2019 may be used either alone or in combination with other aspects described herein. This application is incorporated by reference by its entirety.

In some embodiments, an arrangement of piezo elements (e.g., an array) may be used to provide scent information to a user. Such arrangements may be directly addressable via a controller or other device to control each of the piezo elements. Some embodiments use an array of piezo elements positioned near the nose to provide scent output directly to the user.

In some embodiments, a chamber may be formed near or around the user's nose to permit the user to receive the outputs of the piezo elements. The chamber may be formed, for example, using a housing that substantially surrounds the user's nose and that directs outputs of the piezo elements towards the user's nose. In some embodiments, the housing may be adapted to be mounted to an underside of an existing headset device.

According to some embodiments, the device includes a plurality of piezoelectric elements that are capable of being operated within a number of variable states. Such states may be controlled by a processor such as a microcontroller. The piezoelectric elements may operate as pumps that can be used to drive scents within channels that can be positioned near the user's nose. In some embodiments, these channels may be configured in a variety of configurations using, for example, tubes or conduit, air reservoirs, vessels, and other physical constructs to obtain a system that disperses sent into or near the user's nose.

In some embodiments, an OVR device may include a processor and a serial input provided by a game engine. In some embodiments, an application programming interface (API) may be provided as a programmatic interface by which games and other external programs may be used to control and deliver scent information. By transmitting certain sequences of commands, the OVR device may be capable of delivering a scent output by controlling delivery of the variety of scented medium contained within the vessels. The variety of scented medium can be dispersed singularly or in combination to achieve a realistic sense of an object or environment. In some embodiments, the vessels can be designed to contain the different scented media in liquid, solid or even gel form. The vessels may also contain certain functionality or identifiers that allow them to be identified to the OVR system (e.g., what type of scent, level of media, etc.). In some embodiments, different combinations of vessels may be associated with different game formats. In some embodiments, each vessel is intended to be changed out when the scented media is depleted.

As discussed above, the device, according to some embodiments, may be provided as a companion device or may be fully embedded in a Virtual Reality (VR) or Altered Reality (AR) headset system. According to some embodiments, coupling devices are provided to attach the OVR device to various headset systems, such that outputs of the OVR device are positioned near the user's nose. In other embodiments, the OVR device features may be fully incorporated within the headset system. In one implementation of a fully integrated system, commands used to control OVR functions are integrated within the headset inputs provided by the game engine. In other embodiments, it is appreciated that such an OVR device may be integrated with other inputs and outputs, such as blood pressure monitors, haptic feedback devices, heartrate monitors, eye movement monitors or other devices.

In some embodiments, an atomizer is provided for dispensing liquids into the air. In some implementations, a device is provided for generating atomized fluid specifically, but not exclusively, for production of small droplets of scented oil and other fluid-based fragrances, among other types of liquids. In some embodiments, the device comprises a tube having a proximal opening and a distal opening, wherein media inside the tube is forced out of the proximal opening via an aperture plate.

In some embodiments, the tube further includes at least one piezoelectric plate that is attached to a face of the tube. The device further includes an aperture plate that is attached to the proximal end of the tube whereas the distal end of the tube is connected to a fluid supply source for supplying fluid through the tube to aperture plate at the proximal end of the tube. In some embodiments, the aperture plate includes a plurality of conical apertures that extend through the thickness of the plate.

In some embodiments, the device comprises a tube having a proximal opening and a distal opening, wherein fluid enters the distal end and is forced out of the proximal opening via an aperture plate. In some embodiments, fluid may be existing within the tube and/or added via the distal end, such as by a mechanism to add fluid as the device operates and forces the fluid out. In some embodiments, the device is provided with the fluid located within the tube.

According to at least one aspect, a system is provided comprising a processor, at least one piezoelectric element controllably coupled to the processor, one or more scented media, and an interface adapted to receive one or more commands from an external content processor, wherein the processor is configured to, responsive to the received one or more commands, control the at least one piezoelectric element to deliver an output scent using the one or more scented media.

In some embodiments, the system further comprises one or more vessels that contain respective ones of the one or more scented media. In some embodiments, the one or more vessels each includes a corresponding piezoelectric element that are controllably coupled to the processor. In some embodiments, the one or more commands includes at least one command that selectively controls an identified piezoelectric element to render a specific scent. In some embodiments, the one or more command includes a plurality of commands that selectively control more than one piezoelectric element to render a blended scent.

In some embodiments, the system further comprises a programmable interface through which the external content processor may control the at least one piezoelectric element.

In some embodiments, the one or more commands each specified a duration and intensity value associated with a respective scent. In some embodiments, the system further comprises a housing, the housing comprising a physical coupling to a headset capable of being worn by a user.

In some embodiments, the system includes hardware that delivers an olfactory output to the user, wherein the physical coupling positions the olfactory output of the system proximate to the users nose. In some embodiments, the processor, the at least one piezoelectric element, the one or more scented media and the interface are part of a VR or AR device. In some embodiments, the one or more vessels that contain respective ones of the one or more scented media are detachable from the system.

In some embodiments, the commands from an external content processor are communicated responsive to an interaction of a user in an AR or VR realm. In some embodiments, the external content processor communicates proximity information to the system responsive to the user's interaction with one or more elements in the AR or VR realm.

In some embodiments, the at least one piezoelectric element comprises a tube having a proximal opening and a distal opening, an aperture element coupled to the proximal opening of the tube, the aperture element having at least one aperture, a piezoelectric element attached to a surface of the tube, the piezoelectric element adapted to receive an electrical signal that causes the piezoelectric element to vibrate and induce a wave along a length of the tube that forces a medium through the at least one aperture. In some embodiments, the tube is at least one of a cross-sectional shape of a square, a triangle, a polygon, a rectangle and a circle. In some embodiments, the tube is adapted to receive the medium through the distal opening. In some embodiments, the medium includes at least one of a solid, a liquid and a gel. In some embodiments, the tube is adapted to receive a wick element that delivers a liquid medium to be dispersed. In some embodiments, the piezoelectric element forms a unimorph element with the tube.

According to some aspects, a computer-implemented method is provided comprising acts of receiving, via an interface of a scent generating device, a data element defining at least one scent to be rendered, processing, by a processor coupled to the interface, the received data element, controlling, responsive to processing the received data element, at least one piezoelectric element to deliver an output scent identified by the received data element. In some embodiments, the scent rendering device includes a plurality of scented media, and wherein the received data element uniquely identifies the output scent among the plurality of scented media to be rendered.

In some embodiments, the data element forms a stream of data, and the method further comprises an act of processing a received stream of data, the stream of data defining a plurality of scents to be rendered. In some embodiments, the a data element defining the at least one scent to be rendered defines a duration and an intensity value associated with the at least one scent to be rendered, and wherein the method further comprises controlling, responsive to processing the received data element, at least one piezoelectric element to deliver an output scent responsive to the defined duration and an intensity value associated with the at least one scent to be rendered. In some embodiments, the data element defining the at least one scent to be rendered defines a start command, and wherein the method further comprises an act of processing, by the processor responsive to the start command, one or more scent rendering commands defined by the data element.

In some aspects, a cartridge is provided comprising a plurality of chambers, each having a media delivery channel, each media channel being configured to be coupled to a respective aerosol generator within a scent-rendering hardware unit, and a plurality of scented media, each one assigned to a respective one of the plurality of chambers. In some embodiments, the cartridge comprises a coupling that attaches the cartridge to the scent-rendering hardware unit, wherein the cartridge is a replaceable item and is adapted to be removable from the scent-rendering hardware unit. In some embodiments, each of the media channels includes a respective capillary mechanism per respective chamber to its respective aerosol generator. In some embodiments, the cartridge comprises a component that provides a force to the capillary mechanism that maintains contact between the capillary mechanism and a portion of its respective aerosol generator. In some embodiments, the component that provides force to the wick element includes a spring. In some embodiments, the component that provides force to the capillary mechanism includes at least one of a group comprising microfluidic forces, a physical component coupled to a housing of the cartridge, and a spring. In some embodiments, the wick is in contact with a plate of the aerosol generator, and liquid is transferred from the chamber to the plate of the aerosol generator by capillary action. In some embodiments, the aerosol generator within a scent-rendering hardware unit includes at least one piezoelectric element.

In some embodiments, the cartridge comprises a temporary cap element that is configured to be removed prior to coupling the cartridge to the scent-rendering hardware unit. In some embodiments, the temporary cap element includes one or more seals of a plurality of the media delivery channels. In some embodiments, the temporary cap element includes open cell foam elements that seal a tip of a wick/tube element of the cartridge. In some embodiments, each media channel includes a straw element including a wick element that is configured to deliver scented media to the respective aerosol generator within a scent-rendering hardware unit. In some embodiments, the cartridge comprises a sealing mechanism that creates a seal between an interior surface of each aerosol generator and an exterior surface of a respective straw element. In some embodiments, the respective aerosol generator is a replaceable item and is adapted to be removable from the scent-rendering hardware unit. In some embodiments, the respective aerosol generator is combined with the cartridge and is coupled together in order to be used as a single removable and replaceable unit. In some embodiments, a system is provided that includes a cartridge according to various embodiments described herein.

Still other aspects, examples, and advantages of these exemplary aspects and examples, are discussed in detail below. Moreover, it is to be understood that both the foregoing information and the following detailed description are merely illustrative examples of various aspects and examples and are intended to provide an overview or framework for understanding the nature and character of the claimed aspects and examples. Any example disclosed herein may be combined with any other example in any manner consistent with at least one of the objects, aims, and needs disclosed herein, and references to "an example," "some examples," "an alternate example," "various examples," "one example," "at least one example," "this and other examples" or the like are not necessarily mutually exclusive and are intended to indicate that a particular feature, structure, or characteristic described in connection with the example may be included in at least one example. The appearances of such terms herein are not necessarily all referring to the same example.

BRIEF DESCRIPTION OF DRAWINGS

Various aspects of at least one example are discussed below with reference to the accompanying figures, which are not intended to be drawn to scale. The figures are included to provide an illustration and a further understanding of the various aspects and examples, and are incorporated in and constitute a part of this specification, but are not intended as a definition of the limits of a particular example. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure. In the figures:

FIG. 6 shows example scent classification information that may be used according to various aspects;

FIG. 10 shows an example device that may be used to render scent according to some embodiments;

FIG. 11 shows an example device that may use one or more devices to render various scents according to some embodiments;

FIGS. 16A-16E show various views of an example olfactory stimulus system according to some embodiments;

FIGS. 19A-19F show various views of a cartridge assembly according to various embodiments.

DETAILED DESCRIPTION

As discussed above, some embodiments relate to a new cartridge system that can be used to render scents within an environment. As discussed above, cartridge elements containing a plurality of scents can be controlled to produce complex combinations of scents to be experienced by a user. The cartridge system may have a removable portion that contains scent media, and other portions of the cartridge are coupled to another device placed within a device used for rendering scents to a user (e.g., a device such as a AR/VR headset or other device), As discussed above, cartridge elements containing a plurality of scents are provided for use with, for example, a computer system used in XR (e.g., VR, AR or other virtual environments) as discussed by way of example below.

According to some implementations, an overall system is provided that is capable of rendering scent information to a user. For instance, it is appreciated that there are no adequate commercially-available devices capable of rendering scent information in an XR (e.g., AR, VR or other environment). In particular, according to some embodiments, it is appreciated that it would be beneficial to have a device that could be used with existing AR or VR headsets to render scent information to a user. Such scent information may be rendered by a game engine responsive to activities performed or experienced within the AR or VR realm. In other embodiments, such functionality may be incorporated within such headset devices.

Figure 1:
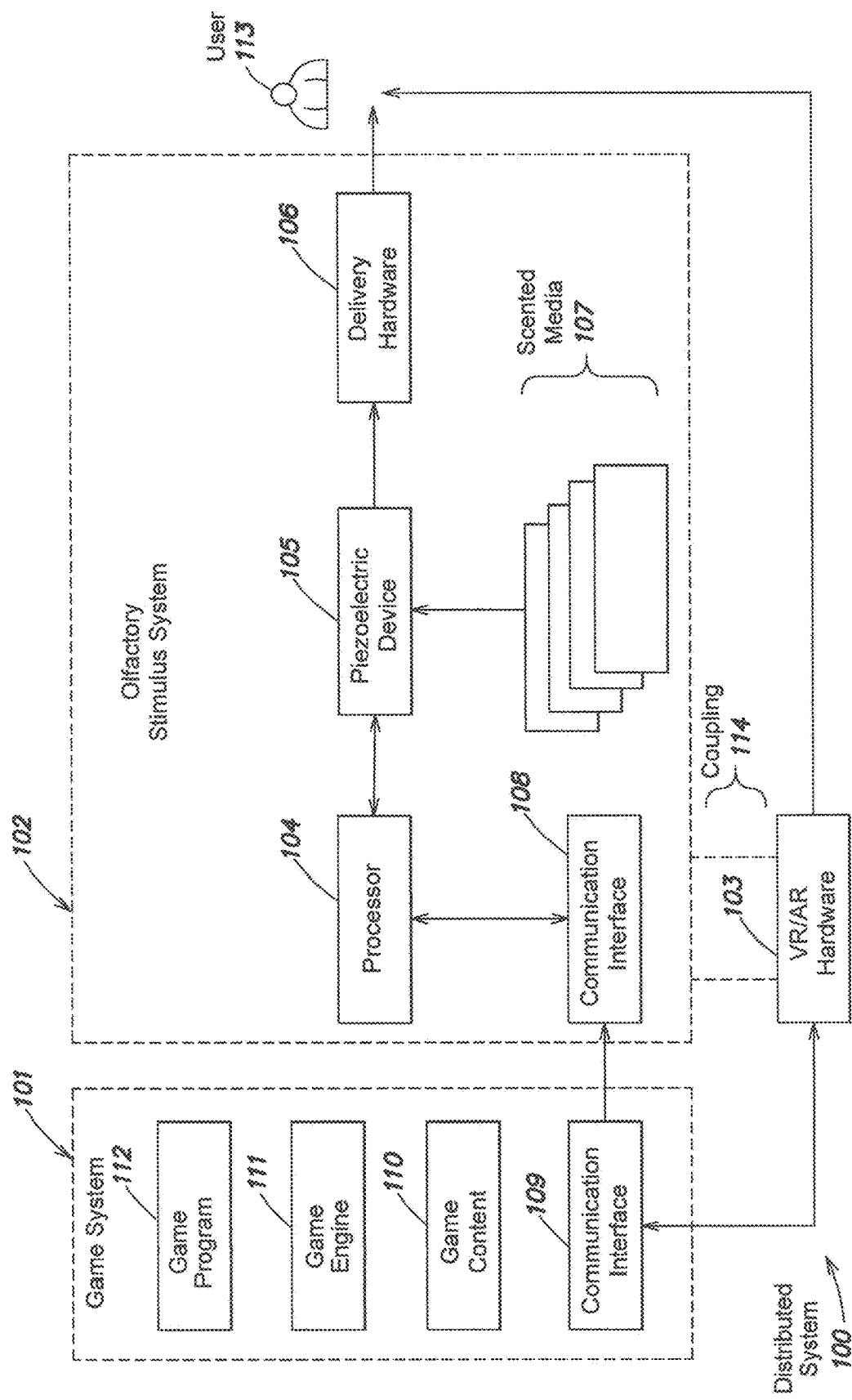
FIG. 1 shows a block diagram of a distributed computer system capable of implementing various aspects.

FIG. 1 shows a block diagram of a distributed computer system 100 capable of implementing various aspects. In particular, distributed system 100 includes a game system 101, and olfactory stimulus system 102, and possibly separate VR/AR hardware, the combination of which are used to communicate information to a user 113.

In particular, game system 101 may include a game program 112, a game engine 111, game content 110, and a communication interface 109. Game system 101 may use the game engine 111 which may include for example, any processors, code, and development platform used to write game programs (e.g., game program 112). Notably, according to various embodiments, game programs may be provided in interface through which they can communicate with an olfactory stimulus system. Such interfaces may include, for instance, an application programming interface (API) that defines commands and data structures for controlling the olfactory stimulus system 102. Further, game system 101 may include one or more communication interfaces 109 which can be used to communicate to system 102. Such interfaces may include, for example, wired or wireless communication interfaces. Although the system may be used with games, it should be appreciated that other types of systems, programs and content may be used, and some aspects are not limited thereto.

System 102 may also include a processor 104 that controls operation of system 102 functions. System 102 may include one or more piezoelectric devices (e.g., piezoelectric device 105) which control the delivery of one or more types of scented media 107 for the purpose of rendering scent information to the user (e.g., user 113). Piezoelectric device 105 may deliver an olfactory output via one or more delivery hardware elements 106. Such elements may include, for example, vessels, interconnecting tubes, reservoirs, venturi elements, inlets, outlets, channels and/or any other active or passive delivery mechanisms. In some embodiments as discussed further below, a cartridge system is provided which houses these scent delivery mechanisms and is part of an overall system for rendering scent information.

Further, as discussed above, the olfactory stimulus system may be provided as part of an existing headset device but in other embodiments, the olfactory stimulus system may be provided as an additional device for existing VR/AR hardware (e.g., hardware 103). To accomplish this, a physical coupling 114 may be provided such that the olfactory stimulus system is positioned such that scent outputs may be provided to a user (e.g., user 113).

According to one embodiment, processor 104 may include a specially programmed microcontroller that performs certain specified control functions. One example of a specific control processor and circuitry is shown by way of example in FIG. 5 discussed below. In some embodiments, the microcontroller (MCU) may include an ATmega328p Arduino-type controller. It should be appreciated, however, other controller types may be used. Further, the microcontroller may also include some additional auxiliary components such as a frequency generator, digital potentiometer and one or more operational amplifiers which may be used to adjust voltage into a variable amplitude fixed frequency current that can be used to control a piezoelectric element.

Figure 2:
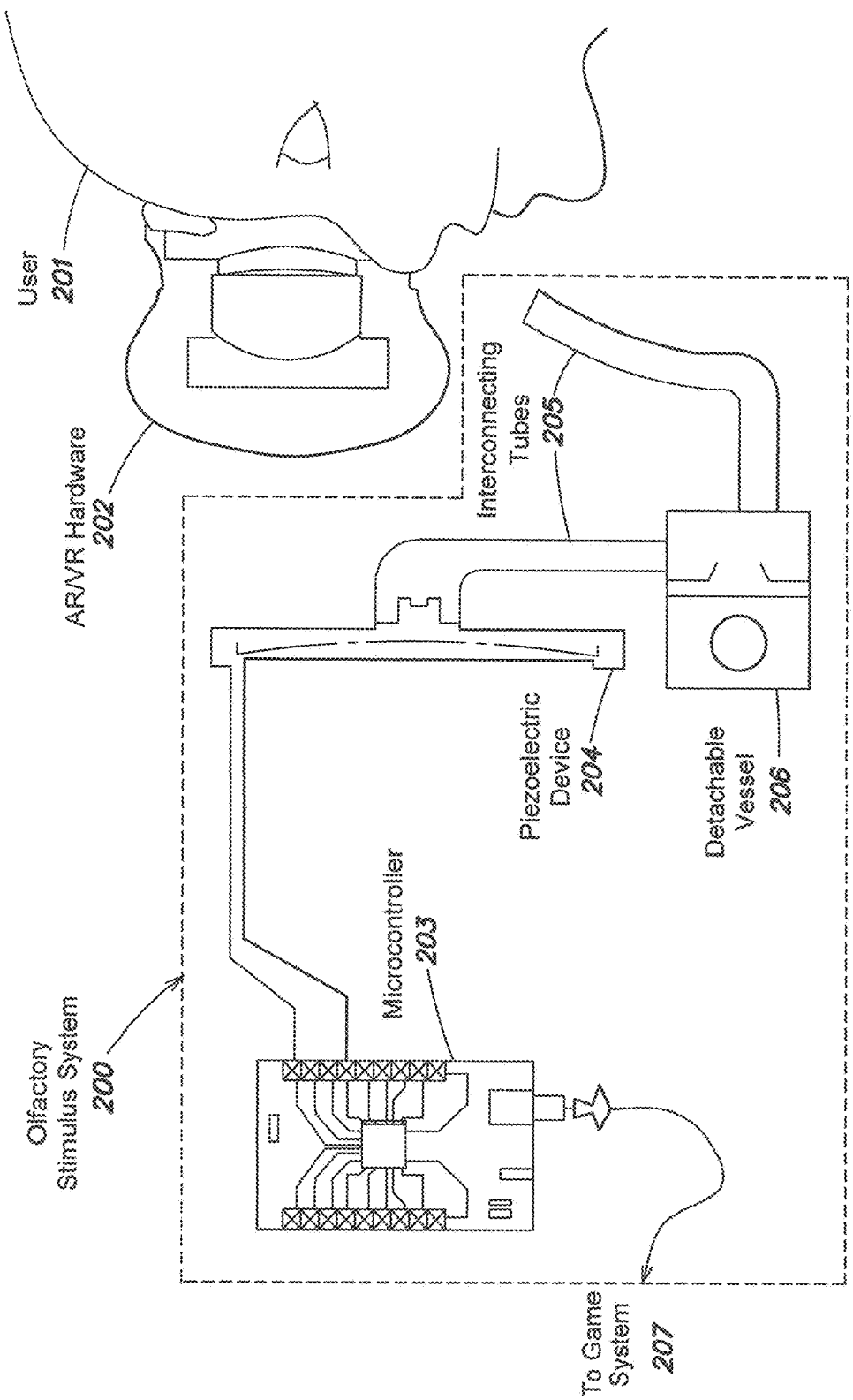
FIG. 2 shows an example olfactory stimulus system according to some embodiments.
Figure 3:
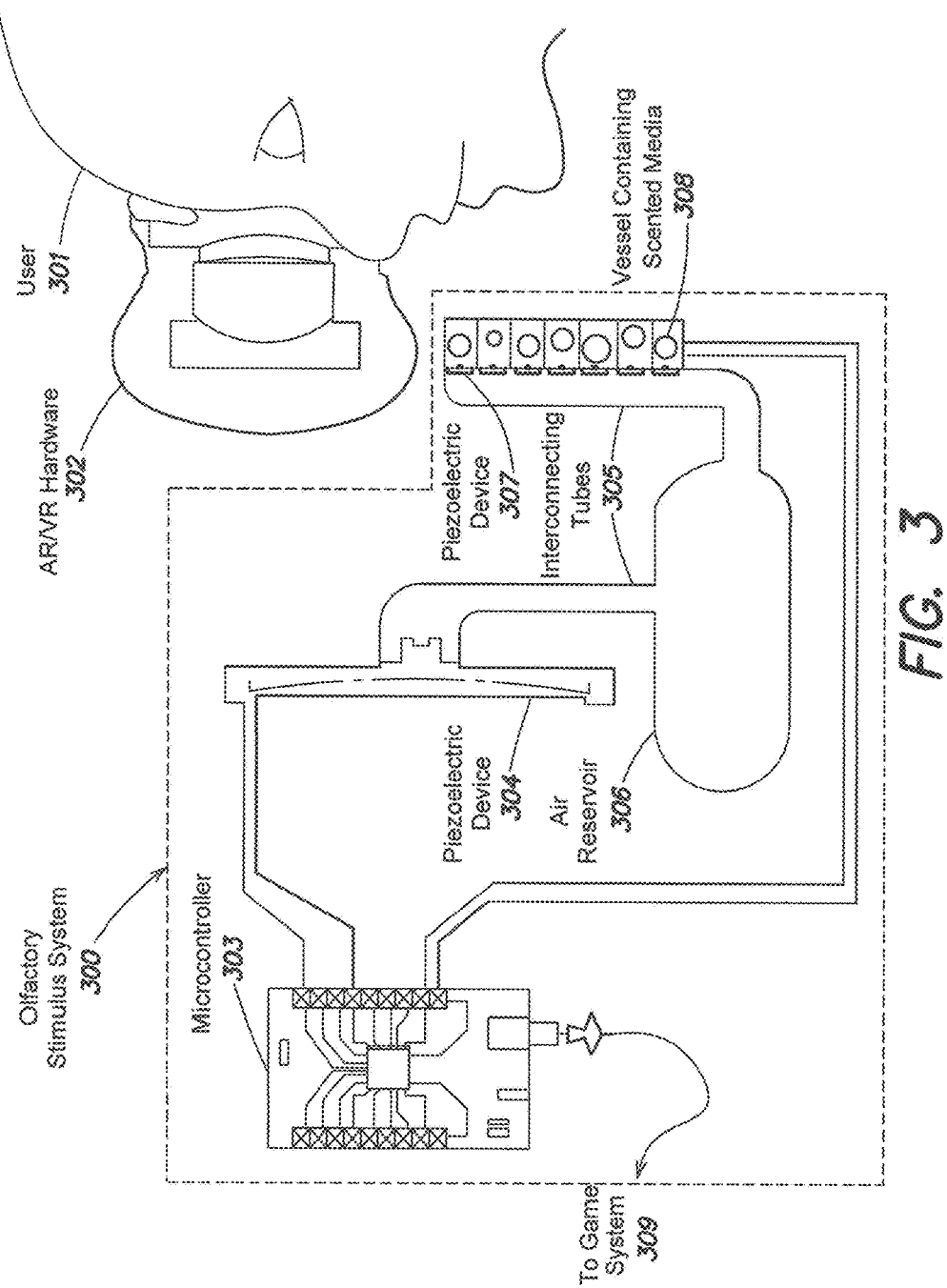
FIG. 3 shows another example olfactory stimulus system according to some embodiments.

FIGS. 2 and 3 show various implementations of olfactory stimulus systems according to some embodiments. In particular, FIG. 2 shows an olfactory stimulus system 200 which can be used with existing AR/VR hardware 202 to present scent information to user 201. System 200 includes a microcontroller 203 that controls a piezoelectric device 204. The piezoelectric device 204 acts as a pump which blows air passed a detachable vessel 206 which contains scent media. Air and/or scent particles are routed between elements using one or more channels such as those provided by interconnecting tubes 205.

According to some embodiments, piezoelectric components may be used to move air and possibly diffuse liquids into a channel. Channels may be constructed using tubes manufactured using chemically resistant materials (e.g., brass or some other material). In some embodiments there may be manufactured using chemically resistant materials to counter the effects of water and possibly mild amounts of alcohol present within the scented media. According to some embodiments, such channel elements may be internally molded and/or printed elements.

Detachable vessel 206 (among other elements and embodiments described herein) may also be made from chemically resistant materials (e.g., glass, Plastic (PTFE, PEEK, UHMW, PTE, possibly HDPE chemically resistant variants), stainless steel, or other material(s) either alone or in combination with other materials).

Further, microcontroller 203 may be coupled to a game system 207 via one or more interfaces (e.g., a communication interface such as a wired or wireless connection (e.g., Bluetooth, Wi-Fi, or other type wireless communication protocol)).

FIG. 3 shows an alternative configuration of an olfactory stimulus system 300. In particular, similar to system 200, FIG. 3 shows an olfactory stimulus system 300 which can be used with existing AR/VR hardware 302 to present scent information to user 301. Similarly, olfactory stimulus system 300 may include a microcontroller 3031 or more piezoelectric devices (e.g. devices 304, 307) interfaces to a game system (e.g., game system 309), and one or more channel elements including reservoirs (e.g., air reservoir 306), tubes (e.g. interconnecting tubes 305), vessels (e.g. one or more vessels containing scented media 308) among other items. Notably, the system may have a two stage design where there are smaller piezoelectric elements provided in addition to a main piezoelectric element that provide the majority of air movement.

Notably, in an alternative configuration shown in FIG. 3, separate piezoelectric devices are provided for specific vessels that contain various scented media. The microcontroller may be selectively controlled to activate certain piezoelectric devices to control delivery of particular scented media. As discussed further below, commands that specifically address particular piezoelectric devices may be provided such that the game system may control delivery of particular scents. In some embodiments, different vessels contain different scents. In one implementation, vessels may contain active logic that communicate their information (e.g., what scents they contain, status, level of media, etc.) with microcontroller 303. Also, in some implementations collections of vessels or individual vessels may be removed and/or replaced when they are exhausted. Air reservoir 306 may be provided such that air pressure may be stored in controlled and selectively delivered to individual vessels to provide a rendered output.

Figure 4:
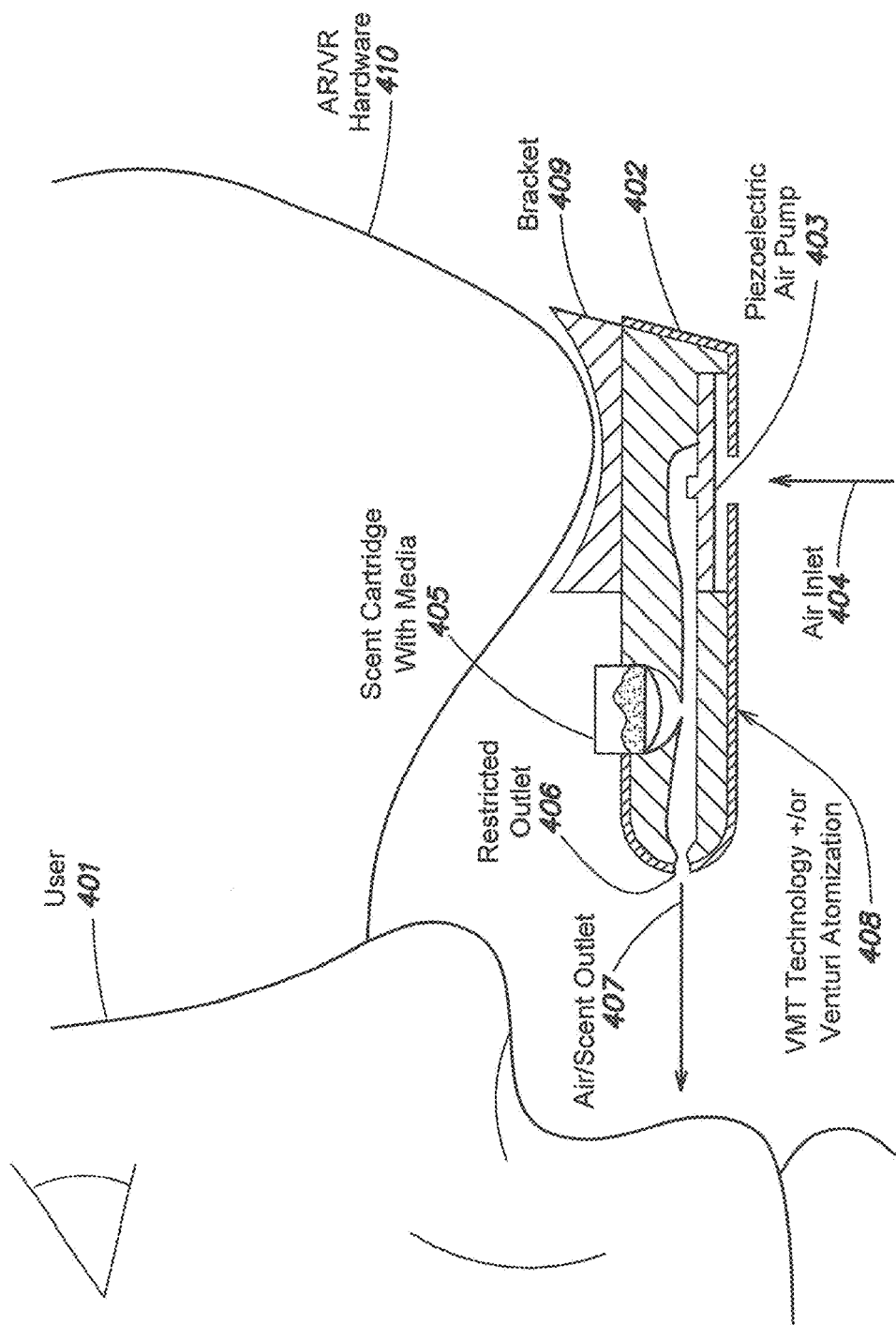
FIG. 4 shows an example olfactory stimulus system physical configuration according to various embodiments.

FIG. 4 shows another example device configuration 402 that may be used alone or in connection with other embodiments. For instance, as shown in FIG. 4, element 402 is connected to existing AR/VR hardware for 10 via a physical bracket 409. Notably, the position of element 402 may be adjusted so that an olfactory output (e.g., air/scent outlet 407) may be positioned near a user's nose (e.g., the nose of user 401). In the configuration shown in FIG. 4, element 402 includes an air inlet 404 a restricted outlet 406 a piezoelectric air pump 403 and venturi technology (e.g., an atomizer nozzle). In particular, the piezoelectric air pump 403 operates to pump air from an air inlet 404 within the chamber which mixes with an output of a scent cartridge having media (e.g., cartridge 405) in the mixture is pumped through a restricted outlet 406 to the nose of the user (e.g. user 401).

Figure 5:
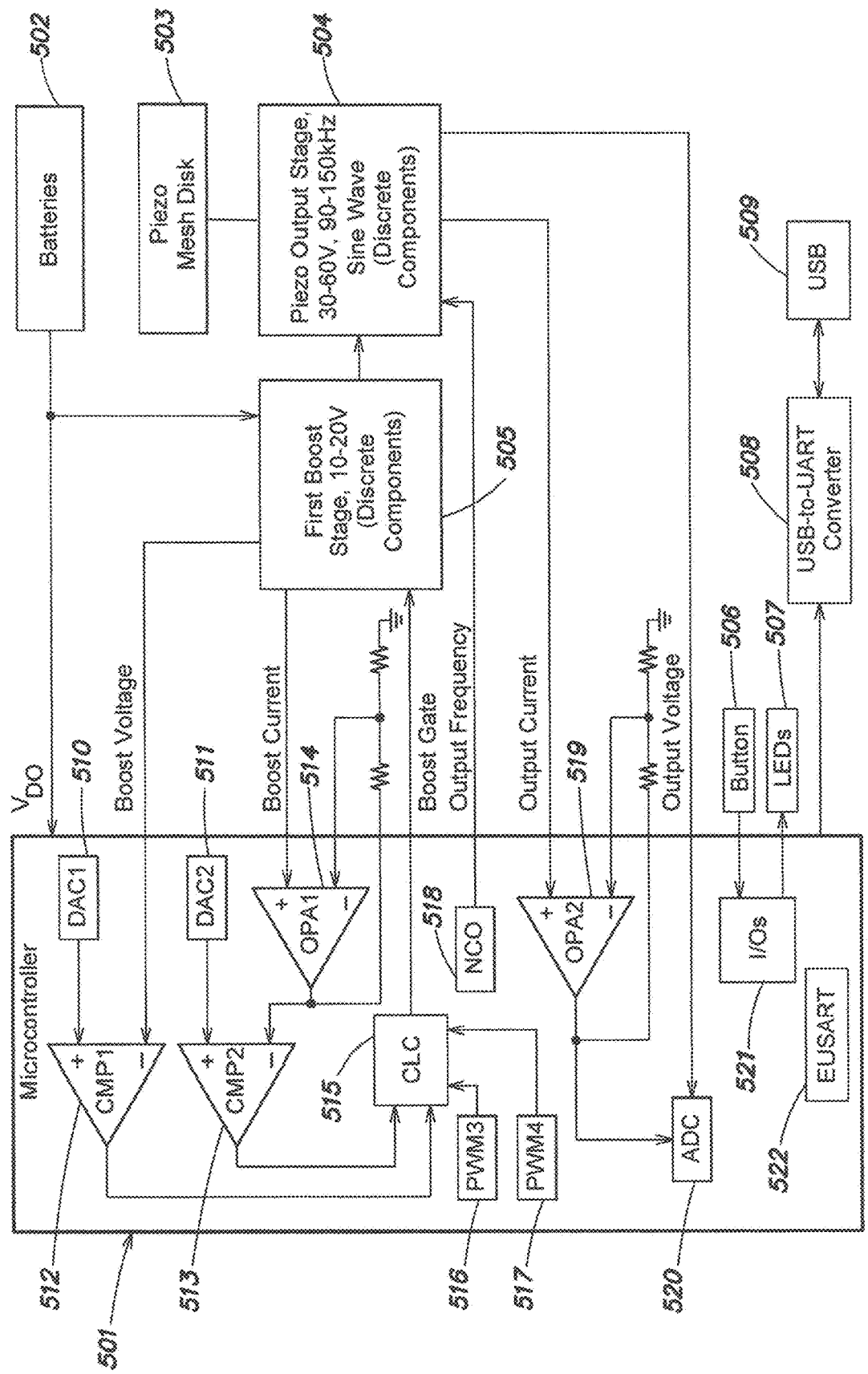
FIG. 5 shows an example control system according to various embodiments.

FIG. 5 shows an example circuit in control function circuitry used to implement various aspects. For instance, a microcontroller 501 may be provided which includes one or more digital to analog converters (e.g., elements 510, 511) one or more comparators (e.g. comparators 512, 513), operational amplifiers (e.g. operational amplifiers 514, 519), Among other elements. As discussed above, the circuit may be used to boost current and voltage and output gate frequency to operate a piezoelectric output stage (e.g., 504) which in turn controls a piezo mesh disk (e.g., element 503) which renders the scented output.

Microcontroller 501 may include one or more I/O ports to communicate information and receive information from various elements (e.g. button 506, LEDs 507). Further, microcontroller may include an element (e.g., EUSART 522) to communicate serial data to outside elements (e.g., such as by converting serially formed UART data to a USB output using a USB-to-UART converter 508 and USB interface 509). Also, in some embodiments, the device may operate on its own power supply which could include batteries (e.g., batteries 502) or some other power input. It should be appreciated that different circuitry may be used having more or less components.

Various embodiments may relate to ways of representing scent information in a distributed system, and encoding and decoding such information. FIG. 6 shows one example implementation including example scent classification information that may be used for communicating scent information in a distributed communication network. It is appreciated that smell architecture may be of great importance when it comes to creating a realistic experience, especially in an AR/VR environment such as those provided in virtual reality, altered reality or telecommunication devices using headsets or other devices.

According to various embodiments shown by way of example in table 600, various types of information may be used to classify or qualify scent information. In particular, a particular sent may include proximity information 601, activity information 602, duration information 603, and appeal information 604.

Proximity

In one implementation, proximity information may be used to express how close the user or player is to an odorant object (e.g., within an AR/VR environment). In one embodiment, the proximity settings dictate whether a smell is "on" or "off"):

Ambient (the foundation)—the overall smell of a particular environment meant to set an emotional tone Burst (walls, floors, lighting, furniture)—the smell of an object or collection of objects noticeable when passing within a particular distance (e.g., 1 meter)

Specific (appliances)—the smell of a specific object noticeable only when within a predetermined range (e.g., 12 inches or less from face or other reference point)

Function: smell may be controlled by one or more functions that define how smell should be released around an object. For instance, a spherical construct may be defined that adjusts the amount of smell depending on the distance from a surface of the object (or point defined in 3D space).

Activity

In another implementation, activity information may be used to express the level of conscious interaction the player is having with the odorant object. It is appreciated that the level of conscious interaction is not necessarily directly linked to the proximity of the player to the object, but generally speaking, the activity may be proportionate):

Passive—most bursts. Smells that are activated by passing by an object that is not necessarily interact-able but plays a role in creating ambience or foreshadowing in the narrative.

Active—when the player interacts with an object deliberately. Either for curiosity or to gain information/solve a puzzle Invisible—smell that is only released upon performing a specific action like opening a bottle or drawer. This characteristic could allow for circumventing the standard proximity protocols Predictive—predictive smells are ones that come on the breeze around a corner or from behind a closed door. They can be literally predictive (fire/smoke) or ever changing to promote a sense of doom.

Causal—The effect when the user takes an exaggerated breath in

Duration in one implementation, duration information may be used to express how long is the smell being activated for in the hardware:

Burst—a burst will generally be a release of a predetermined time (e.g., 1 second) of a single or series of heavily diffusive aromas. Navigating through the VR environment will also be navigating through different bursts. The pockets of scent experienced in succession through space and time will create an aromatic tapestry potentially as rich as the visual one.

Sustained—A slow continuous release of scent to either block outside odor or create subconscious reaction. Very faint.

Undulating—a single smell meant to be experienced over a longer period of time so due to the "habituating effect" of the olfactory system it is necessary to increase and decrease intensity in a set predictable manner.

Intervals—a way to mimic smell intensity by modulating rapid micro bursts.

It should be appreciated that other types of encoding scent information may be used, and some embodiments may use different types of encoding. Aspects described herein may also be practiced alone or in combination with systems and elements described in U.S. patent application entitled "SYSTEMS AND TECHNIQUES FOR GENERATING SCENT" filed Sep. 24, 2020, incorporated by reference herein in its entirety.

Figure 7:
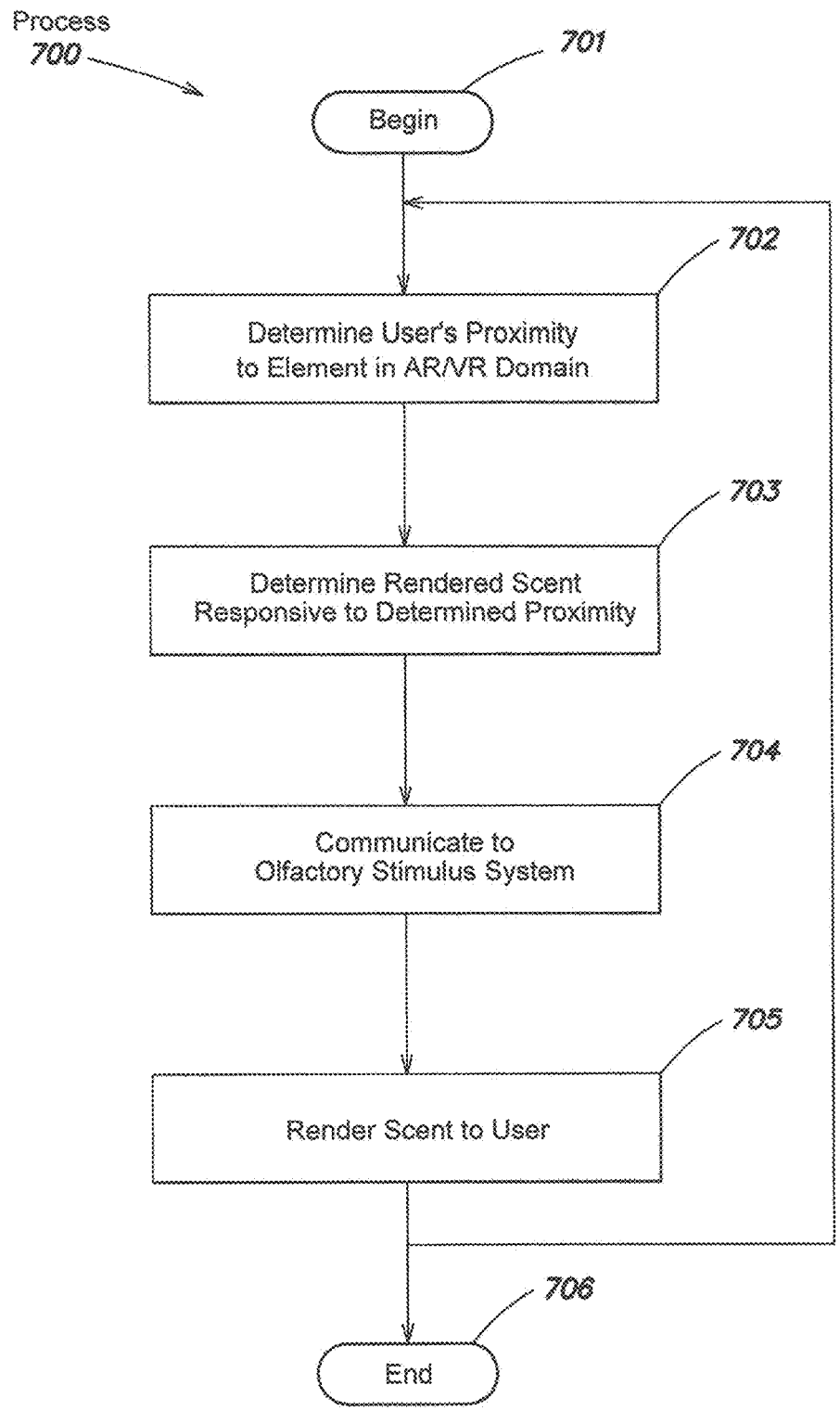
FIG. 7 shows an example process for rendering scent information according to various aspects.

FIG. 7 shows an example process for rendering scent information according to various aspects. At block 701, process 700 begins. At block 702 the user's proximity is determined in relation to an element in an AR/VR domain. For instance, the game engine while executing the game code may monitor the user's proximity to one or more virtual elements such as environmental elements, game elements or other surface or object. At block 703, the system may determine a rendered scent responsive to the determine proximity between the user and the element. For example, if the user is within a certain proximity of a surface that has a scent associated with it, the executing software may determine a scent to be "played" to the user at some point in time during the game execution or other contact rendering to the user. At block 704, the system communicates control information indicating the sent to be rendered to the olfactory stimulus system. Such information may include any type of encoding information, such as a duration of a scent to be rendered, an intensity value or other information. Such information may be transmitted, as discussed above, over a wired or wireless communication link between a content providing system and the olfactory stimulus system. At block 705, the olfactory stimulus system renders the scent to the user. At block 706, process 700 ends, although it is appreciated that this process may work as a continuous loop as the user is experiencing the AR/VR content.

Figure 8:
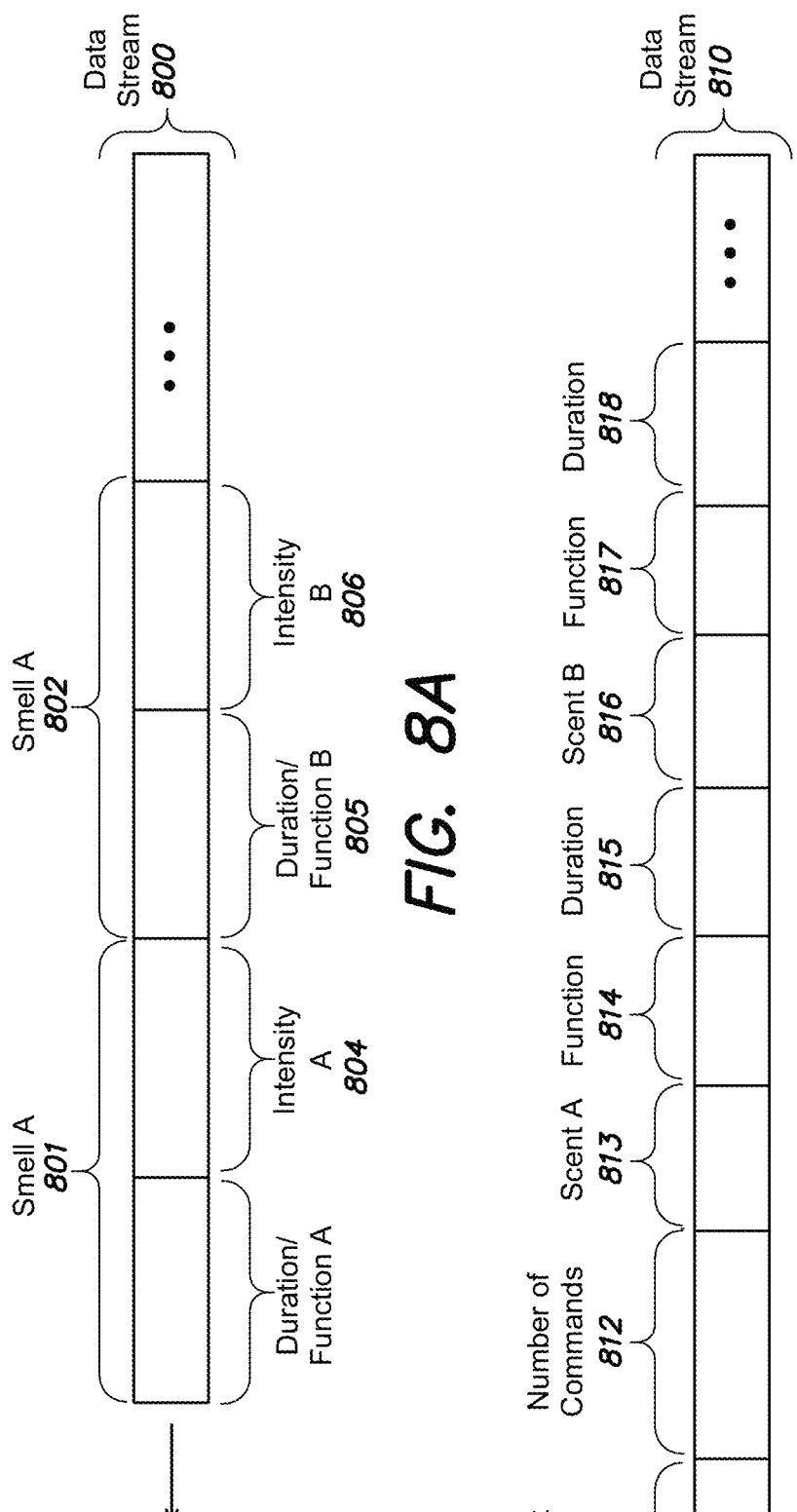
FIGS. 8A-8B shows example data formats for communicating scent information according to various embodiments.

FIG. 8A shows an example format for communicating scent information according to various embodiments. As discussed above, the olfactory stimulus system may be capable of receiving a data stream (e.g., data stream 800) sent from a game engine or other content providing system for the purpose of communicating smell information. As shown, the data stream may include one or more pieces of information that correspond to particular smells to be rendered to the user.

For instance, a portion of information corresponding to smell A (e.g., item 801) may be transmitted serially from the content provider to the olfactory stimulus system. Data element 801 may include a number of fields, characteristics, and/or values that qualify a particular smell. Element 801 may include specific information that identifies which smell to be played, what duration, in what intensity. Data element 801 may include additional information encoded that reflects how the sent is to be delivered to the user. In some embodiments, element 801 includes a duration/function for smell a 803. Such information may include a value that specifies the duration, as well as a specific identification of smell A. Further, element 801 may include an intensity value A 804 that numerically represents a played intensity of the identified smell. The system may be capable of transmitting multiple smells, or a single scent made up of a combination of individual smells. (e.g., Smell B 802 with duration/function B 805 and intensity B information 806).

FIG. 8B shows another example format for communicating scent information according to various embodiments. As discussed above similar to the system described above with reference to FIG. 8A, the olfactory stimulus system may be capable of receiving a data stream (e.g., data stream 810) sent from a game engine or other content providing system for the purpose of communicating smell information. As shown, the data stream may include one or more pieces of information that correspond to particular smells to be rendered to the user. Notably, data stream 810 may be a different format which is communicated to the olfactory stimulus system when the scent is needed such that data is not continually sent and need not be processed when scent should not be present. In such a format, the data stream 810 (e.g., a partial stream or finite string of data) may be sent to the olfactory stimulus system.

Data 810 may include a start byte 811 that appears at the start of the message and which indicates to the olfactory stimulus system (e.g., a microcontroller operating the olfactory stimulus system) to start processing remaining bites and the string or partial stream of data. In a resting state, a microcontroller of the olfactory stimulus system may be constantly for receipt of a start byte (or other header type or indication). The second portion of the message includes a number of commands 812 which indicates the number of scents in the stream, and which indicates how long the stream will be. Following data element 812 are the actual scent indications to be rendered (e.g., scent A, scent B, etc.). Each of the scent indications includes, for example, a scent label or designation (e.g., an encoded form of Scent A placed within data element 813), a function state of the scent (e.g., an intensity, delivery pattern, etc. for the scent encoded in data element 814), and a duration of the scent (e.g., element 815). Each of the various scents to be rendered may include respective function and duration information encoded within the data stream.

It should be appreciated that smell information may be communicated in real time between entities for the purpose of delivering a realistic environment. Such information may be transmitted in parallel with AR/VR environment information, and in some embodiments, there may be a coordination protocol that synchronizes such information.

Figure 9:
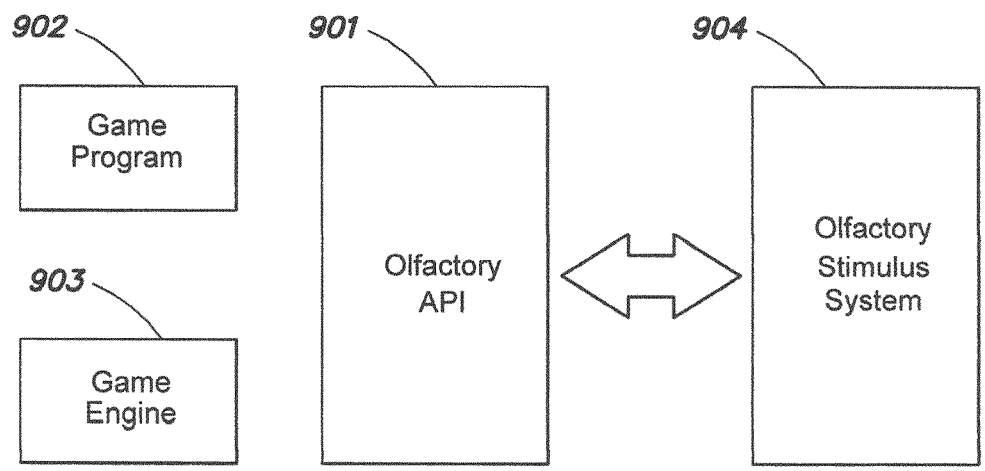
FIG. 9 shows an example software architecture according to some embodiments.

FIG. 9 shows an example software architecture according to various embodiments. In particular, game program 902 and game engine 903 may be capable of communicating to the olfactory stimulus system 904 via an olfactory API 901. Olfactory API 901 may provide functions, interfaces, and parameters through which the game program 902 may communicate with the olfactory stimulus system 904. Further, in some embodiments, communication through the API may be bidirectional, in that information may be received from the OVR system. For example, a status of the OVR system may be communicated and may be visible to a content providing application. For example, whether the OVR system is functioning, has appropriate and suitable levels of media, etc. may be provided to another computing entity.

In a practical example, when someone encounters an object in VR there are things that occur on the game software/drivers side of the game and then there are things that happen on the hardware/firmware side of the game. On the software side, a player interacts with an object based on proximity to that object. The user's proximity to an object generates a value in the gaming engine. Other objects may distort that proximity value such as a wall or wind effects.

The value (whether or not it is modified) is then formatted into a string of characters by the API. That string of characters is then passed on to the microcontroller via USB or Bluetooth or LAN/WAN/Wi-Fi or any other digital wired or wireless communication link. In one example implementation, the system is connected via USB. The string's length is determined by the multitude of scents. In some embodiments, the more scents there are to be rendered, the longer the data string sent over the digital connection.

On the hardware side, the string of characters is then relayed to the microcontroller and is interpreted by the firmware (e.g., residing on the memory of the controller). The firmware selects a mode in which the smell will be delivered and then finally executes an amplitude on the piezoelectric value system(s) which is based on the proximity value generated from the software side. In one implementation, the entire process can be performed about 10-100 times per second and updates the amplitude of the scent as a user interacts with the VR environment and the predetermined or tagged objects in that environment. VR objects can be tagged during the development of the game by a game designer or post compilation of a game through the use of computer vision algorithms during game play.

It should be appreciated that the system, mechanical implementation, software and controls may have a number of features that are usable either alone or in combination with other features. For example, in another implementation, the system may be capable of limiting "brown smell" or residual smells produced as a byproduct of playing previous smells. One example process for eliminating brown smell includes several methods. This first method includes using scent formulas and controlled atomization sizes which are highly dispersive and do not stick to surfaces very well. This ensures that the scent will clear away in a relatively short amount of time. A second process includes restricting the outlet size orifice near the scent cartridge which creates a passive high pressure area. This functions as a passive gate to keep additional scent molecules or atomized clumps from exiting the outlet when the piezoelectric devices are in a resting state. Essentially this function acts as the brakes to the scent delivery mechanism. The third function is to maintain control over the particle release size (nominally 20-2 μm in size). Maintaining particle size may be accomplished, for example, through a VMT, venturi and/or other dispersion mechanisms. It should be appreciated that other features may be provided according to other implementations.

FIG. 10 shows another example device that may be used to render scent according to some embodiments. For example, FIG. 10 shows a piezoelectric device 1000 that may be used to render scent information. Device 1000 may be relatively small in size (e.g., 1-2 cm in diameter, or other size) such that it may be used in a personal scent rendering device such as that shown by way of example in FIG. 11. Device 1000 may be circular in form, and include an area 1001 where scent is released. Device 1000 may include scent media either embedded within the device, or the device is capable of receiving scented material from a channel, or reservoir (e.g., in liquid form). Device 1000 may be operated by providing an activating signal through one or more electrical leads (e.g., leads 1002).

FIG. 11 shows an example device 1102 that may use one or more devices to render various scents according to some embodiments. In particular, device 1102 may be adapted to receive one or more piezoelectric elements such as those shown by way of example in FIG. 10. Further, device 1102 may be adapted to attach to an AR/VR headset (e.g., AR/VR hardware 202). For instance, device 1102 may be adapted to mount to an AR/VR headset via a mounting plate 1101. Device 1102 may be affixed to the headset via one or more attachment elements such as screws, mounts, adhesive elements, or similar elements. Device 1102 may include one or more openings 1103 through which scent is rendered. Because device may be mounted near a lower surface of the headset, the openings of device 1102 may be positioned near a user's nose. Device 1102 may be arc-shaped such that the openings are positioned substantially around an area near the user's nose.

Figure 12:
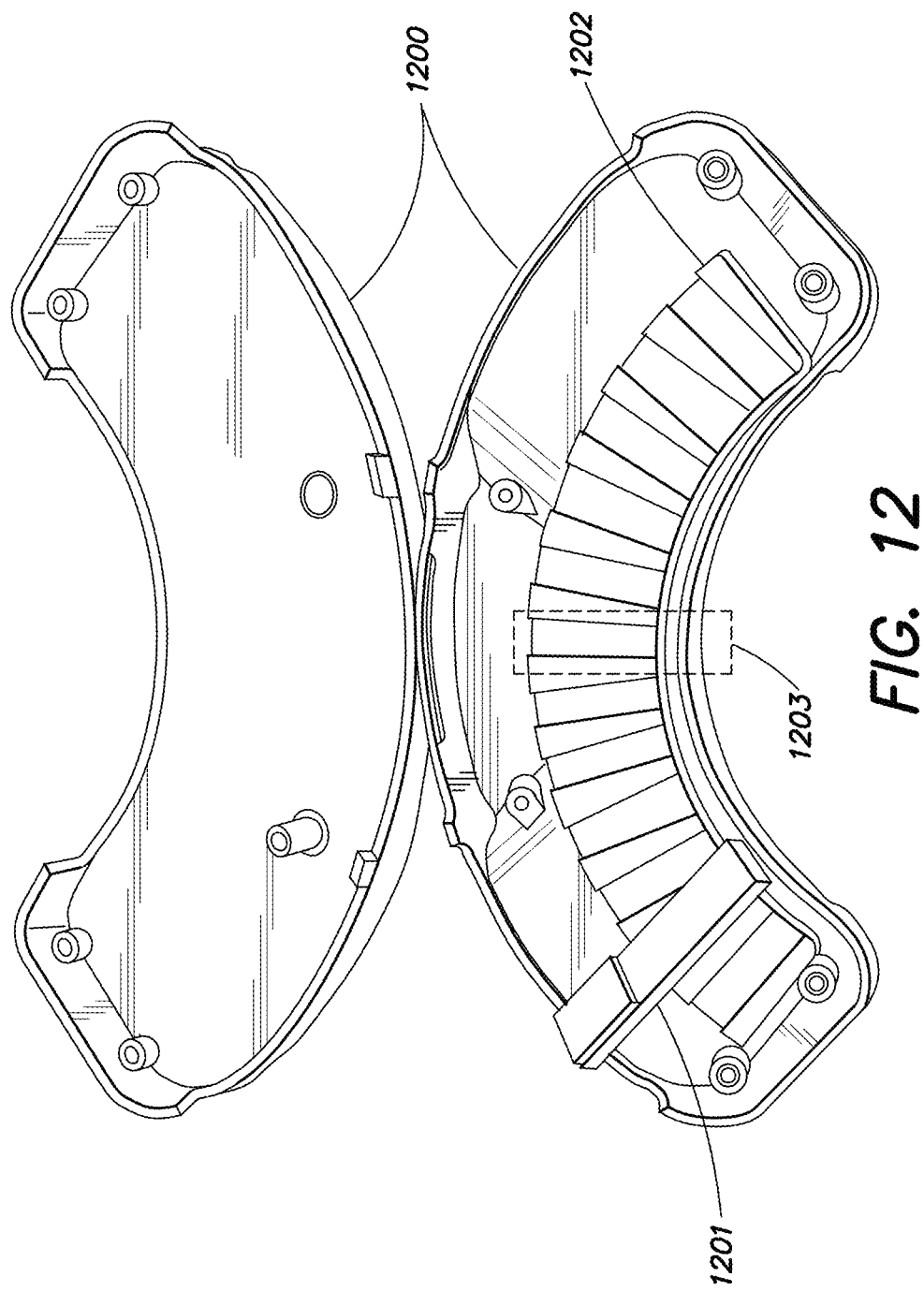
FIG. 12 shows another device that many be used to render various scents according to some embodiments.
Figure 13A:
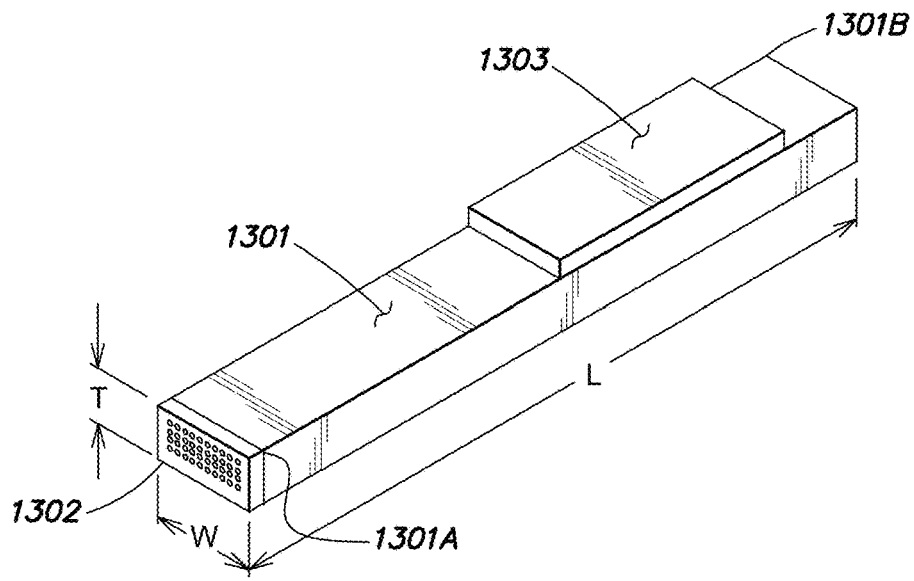
FIGS. 13A-13D show a device for generating atomized fluid according to some embodiments.
Figure 13B:
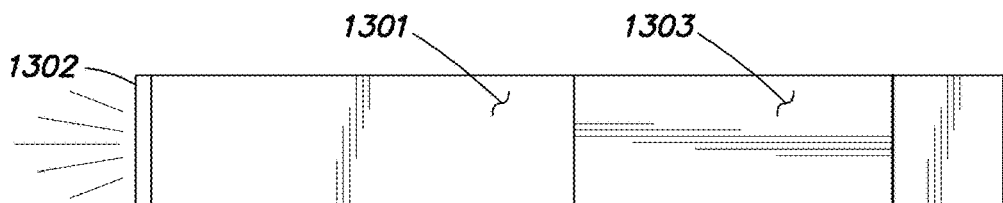
Figure 13C:
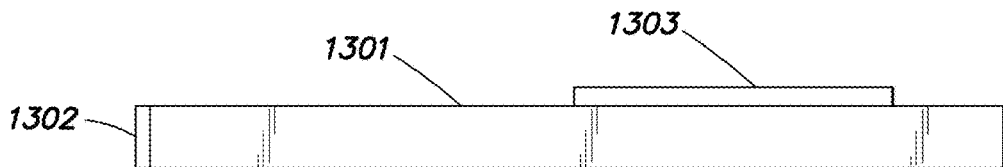
Figure 13D:
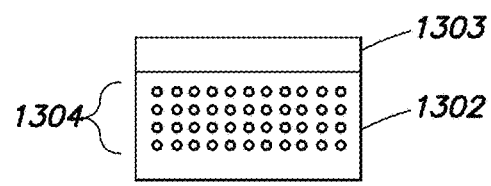

FIG. 12 shows another device 1200 that many be used to render various scents according to some embodiments. Similar to device 1102, device 1200 may be arc-shaped and may be adapted to be attached to an AR/VR headset. Also, device 1200 may be adapted to receive one or more piezoelectric elements (e.g., piezoelectric element 1201). In some embodiments, such elements may be rectangular in shape, and as discussed below with respect to FIGS. 13A-13D, they may be configured to atomize a fluid and project the atomized fluid out of an end of the tube towards a user's nose. Several piezoelectric elements may be arranged in an arc of the device 1200. The elements may be held in channels (e.g., channel 1203) by a holding element 1202. In some embodiments, the holding element may be manufactured using a rubber-like material to isolate the elements and their vibratory effects from one another and the main housing of device 1200. In some embodiments, the piezoelectric elements are sandwiched between several holding elements, thereby positioning and holding the piezoelectric elements within their respective channels. The piezoelectric elements may be adapted to render different scents. Each of the elements may be selectively activated by a controller that sends activating signals to a particular selected element.

FIGS. 13A-13D show a device for generating atomized fluid according to some embodiments. In particular, FIGS. 13A-13D show some embodiments of a device for generating atomized fluid. The device comprises a rectangular tube (1301) having a cross-sectional shape a width (W), a depth (T) and a length (L). A piezoelectric plate (1303) is attached across the width (W) of the tube. In some embodiments, the piezoelectric plate (1303) may be attached to the rectangular tube (1301 via glue, epoxy, solder or other adhesive. It should be appreciated that although a rectangular tube is shown, other shapes of tubes may be used (e.g., circular, triangular, square, etc.).

An aperture plate (1302) is attached to an end of the tube (1301A) while a second end (1302B) is open and is configured to receiving a fluid and supplying the fluid to the aperture plate (1302) through the tube. The piezoelectric plate (1303) is connected to a circuit that generates an electrical signal at a frequency that is equal to the resonance frequency of tube and in an amplitude that is sufficient to produce a flow of atomized droplets. The electrical signal may be, in some embodiments, an alternating signal that is applied to contacts of the piezoelectric plate 1303.

In one embodiment, the tube is made of brass and has a width of 6.35 mm, a depth of 3.125 mm, and a length of 40 mm, with a resonance frequency of 50,000 Hz. It should be appreciated however, that other dimensions, configurations and resonant frequencies may be used. In some embodiments, the piezo element and tube form a unimorph device including an active layer (e.g., the piezo element) and an inactive layer (e.g., the tube surface). One implementation includes a tube having a rectangular or square in shape. In some conventional piezo elements, they may use a pinching/squeezing mechanism to deliver liquids, however, in some embodiments as disclosed herein, a medium (e.g., a liquid) is aerosolized via perpendicular acoustical waves induced by a piezo element.

In some implementations, there are a few ways that the medium can come into contact with the plate:

Free in housing—the liquid is just free in the tube and capped at the end opposite the aperture plate end to seal inside. The vibration pattern forces the liquid in contact with the plate.

Wick—A wick is placed in the tube and capped in with the liquid to force the correct capillary action to move the liquid to plate in conjunction with the vibration. In some embodiments, the wick may be shaped to fill the area within the tube (e.g., a rectangular, tubular, or square shape). In some implementations, the wick element may be a replaceable item, and may be accessible to be replaced. The wick may also be part of or coupled to a reservoir that holds liquid to be dispersed. The wick may be, in some embodiments, bidirectional or unidirectional wicking material made out of, for example, natural fibers and/or synthetic fibers including cotton, polyethylene, nylon, metal, graphene, among others.

Cartridge—A cartridge of custom design is inserted into the back to the tube with a connection point to the tube and plate. The cartridge may, or may not, use a wick or material that has a wicking property. As discussed further below, some aspects relate to a cartridge system which includes aerosol generator devices and a removable portion that includes one or more scented media.

Figure 14:
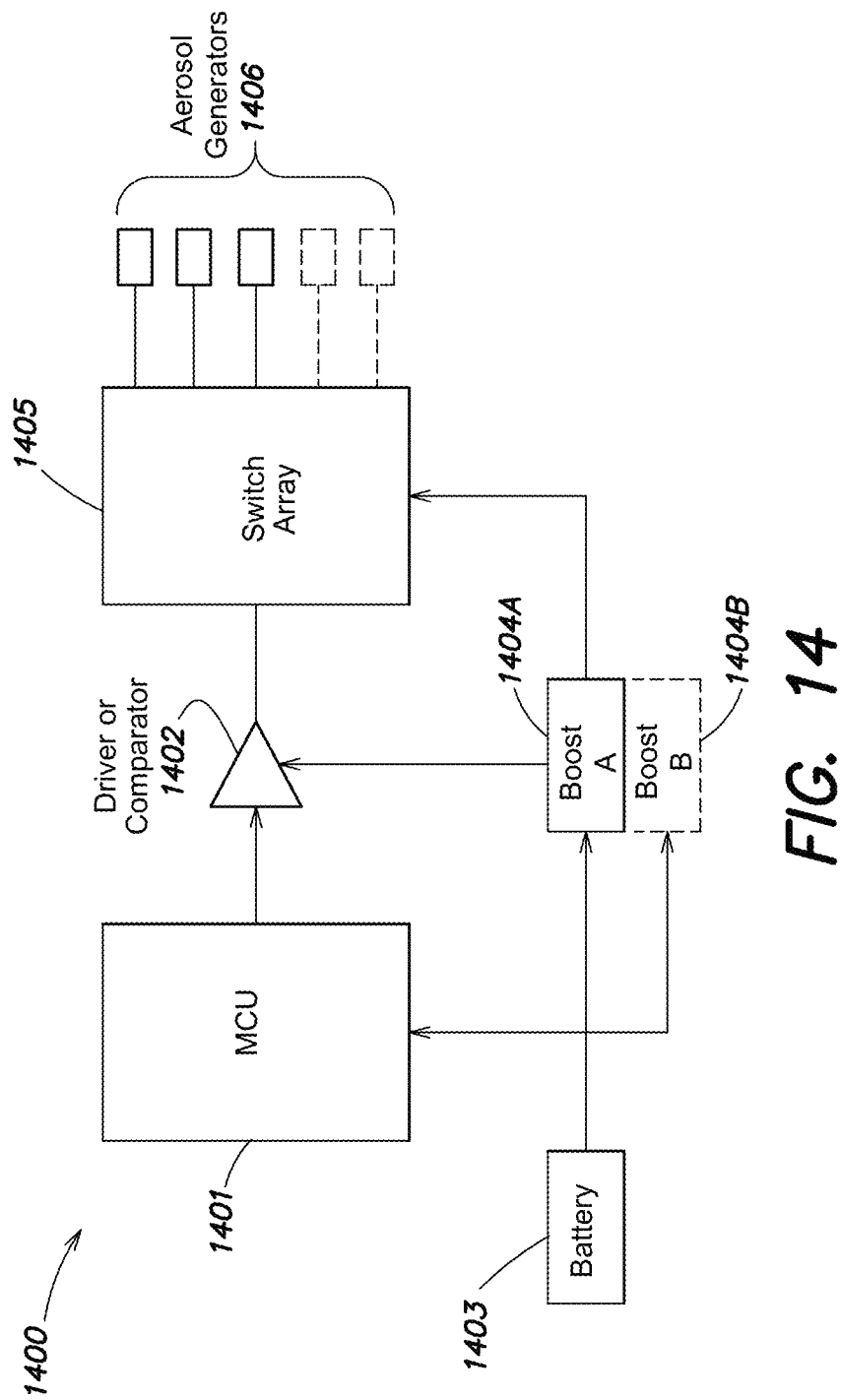
FIG. 14 shows an alternative control system according to some embodiments.

FIG. 14 shows an alternative control system according to some embodiments. In particular, one or more alternative control systems may be used in some embodiments where the piezo device includes one or more tube structures arranged in an array. The circuit may operate, for example, similarly to the system described above with respect to FIG. 5, which performs similar functions. In particular, a device driver circuit may be used to selectively activate different piezo elements (e.g., in an array) according to what scent is addressed (e.g., within a received stream of commands).

In particular, generally within the driver circuit shown in FIG. 14, a microcontroller generates a frequency which is then amplified in power greatly in order to drive selected piezo elements. Switches may be used to control the activation of the amplified power signal. The signal itself can be, for example, a signal of a fixed frequency with a 50% duty cycle. However, it should be appreciated that parameters of the signal (e.g., shape, length, height, pattern, etc. of the signal waveform) may be selectively varied to produce different intensities and lengths (e.g., duration) of scent production. Further, it should be appreciated that a DC signal may be used which includes positive signals or alternatively an AC signal may be used consisting of both positive and negative signals.

FIG. 14 shows a general circuit design which includes several subcomponents including a battery (e.g., battery 1403), a microcontroller (e.g., MCU 1401), a power conversion "boost" (e.g., via boost device A, boost B (elements 1404A, 1404B) and a switching array (e.g., switching array 1405). Optionally, a driver or comparator (e.g., a MOSFET comparator, e.g., element 1402) may be used to drive the logic coming from the MCU to a higher or lower power level to drive the switching array. Also, optionally a secondary power conversion may be used in order to provide a power source used to drive a second logic level voltage. The switching array 1405 is adapted to receive serial signal and convert that signal into the actuation of a specific channel. Each channel coming from the switch array is used to drive each of the individual aerosol generators (e.g., generators 1406). In some embodiments, the array should be sufficiently fast and rated for the appropriate voltage and current in order to be able to drive the aerosol generators in a real-time manner.

Figure 15:
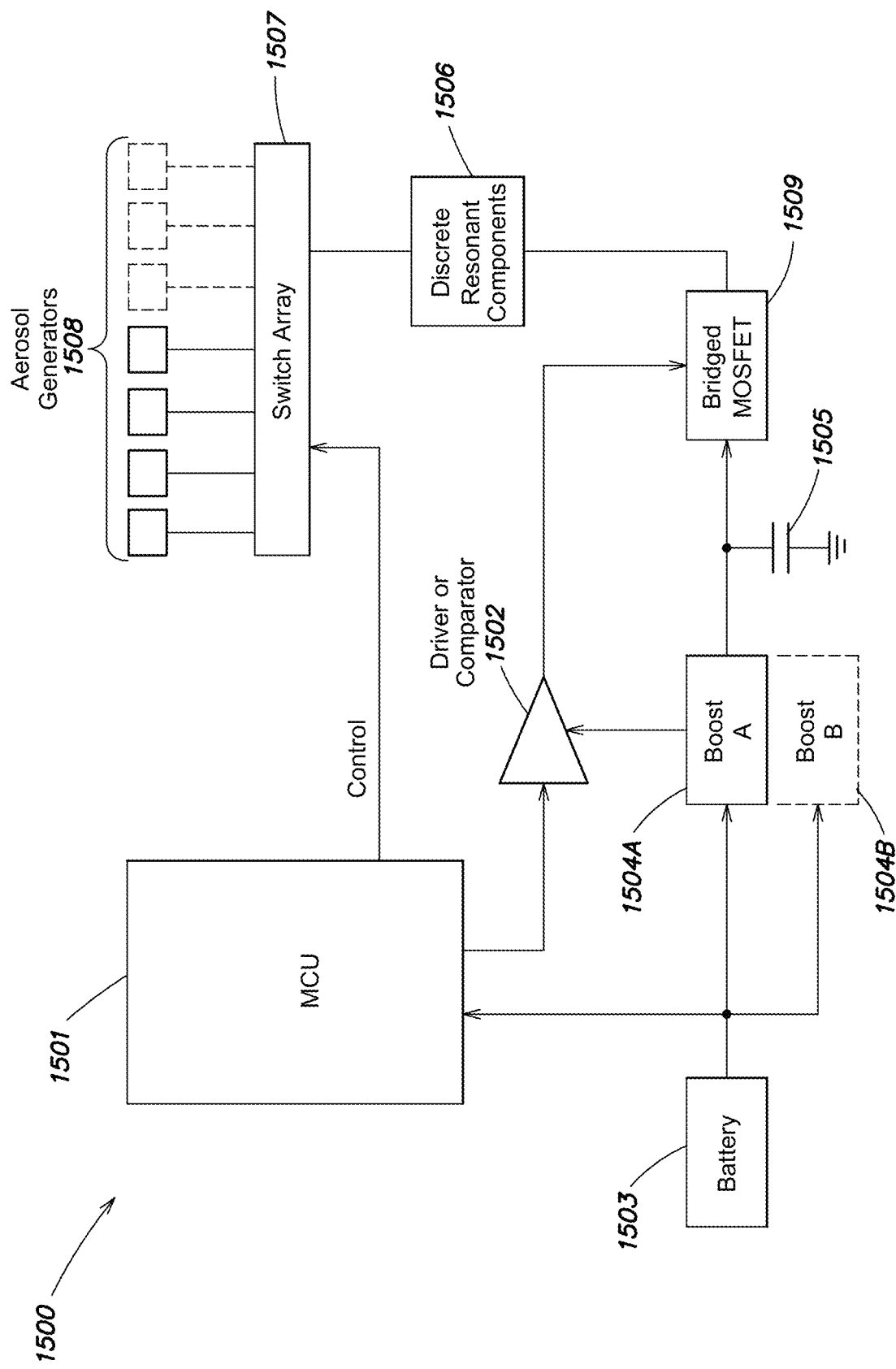
FIG. 15 shows another alternative control system according to some embodiments.

FIG. 15 shows another alternative control system according to some embodiments. In particular, FIG. 15 shows a general circuit design which includes several subcomponents including a battery (e.g., battery 1503), a microcontroller (e.g., MCU 1501), a power conversion "boost" (e.g., via boost device A, boost B (elements 1504A, 1504B), a bridged MOSFET (e.g., element 1506) and a switching array (e.g., switching array 1507). Optionally a driver or comparator (e.g., a MOSFET comparator, e.g., element 1402) may be used to drive the logic coming from the MCU to a higher or lower power level to drive the switching array and or the bridged MOSFET. In some embodiments, optional discrete resonant components (e.g., discrete resonant components 1506) such as capacitors/inductors can be used for further power amplification and signal smoothing. In the circuit shown in FIG. 15, the bridged MOSFET takes signals, (typically in the form of a timed frequency with a duty cycle) from the microcontroller and then amplifies that signal to a higher power level. The switching array is then opens a channel in which the power signal coming from the half bridge can then actuate the aerosol generators with the assistance/amplification of the resonant components.

Figure 16E:
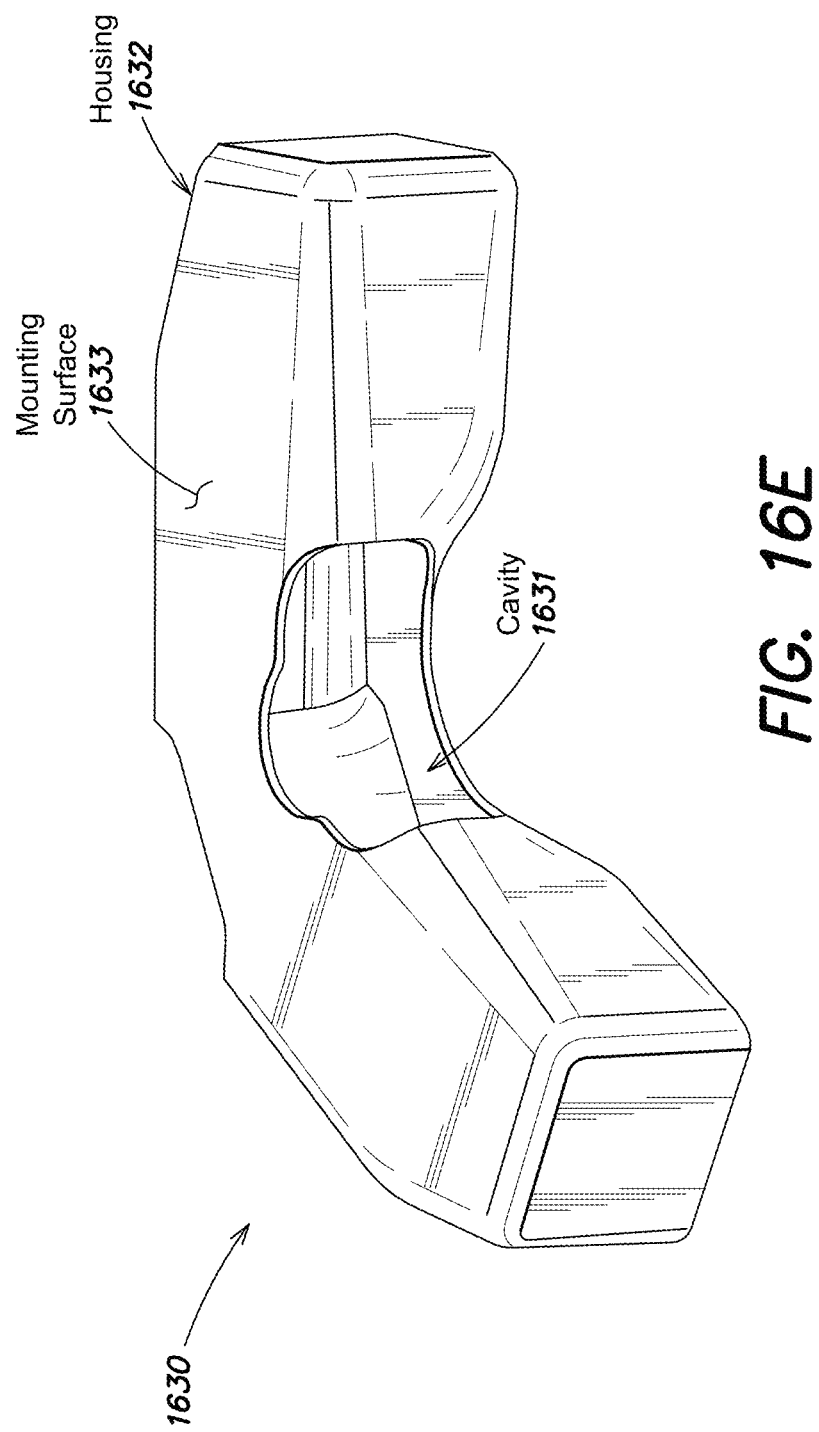

FIGS. 16A-16E show various views of an example olfactory stimulus system according to some embodiments. In FIG. 16A, an example olfactory stimulus system 1600 is shown which includes an L-shaped housing including a number of different components similar to those discussed above with reference to FIG. 1. In particular, system 1600 includes one or more piezo elements and in some embodiments, the Piezo elements take the form of tube—shaped aerosol generators (e.g., elements 1602).

In some embodiments, the elements are arranged within a tube array 1601. The piezo elements may be electrically connected to a PCB 1603 which includes one or more circuit elements such as those discussed above with reference to FIGS. 14-15. System 1600 may include a battery 1604 that is used to power one or more components and generate signals that may be used to drive the production of scent by one or more aerosol generators. Outputs of the tube array 1601 may be positioned abutting a chamber 1605. As discussed further below, a user's nose may be positioned within an opening of the chamber in order to receive one or more outputs of the tube array. In some embodiments, the individual tubes, their media, and/or the array may be a removable and replaceable item (e.g., to renew exhausted media).

At an opposite and of the system, there may be an exhaust 1607 which is used to remove sent from the chamber 1605. Near the output of the exhaust may be positioned a fan element 1606 (or other air moving device) which can be configured to move air in and out of the chamber from the exterior of the system 1600. Notably, it may be useful to clear sent away from the chamber as well as mix outside air with scents produced by one or more of the aerosol generators.

FIG. 16B shows a device 1610 similar to system 1600 whereby a cover 1611 encloses the elements within device 1600. Cover 1611 is attached to the remainder of the housing via one or more attachment element 1612. Cover 1611 encloses the chamber whereby outside air is input via exhaust 1613 or sent is removed from the chamber via the exhaust 1613.

FIG. 16C shows a three-dimensional view of a device that is similar to that shown in FIGS. 16A-16B. In particular, FIG. 16C shows a device 1620 that shows a three-dimensional tube array 1621 including as shown, 12 different aerosol generators positioned within the array. In some embodiments, the tubes are vibrationally isolated from each other such that vibration induced in one tube will not be translated significantly to another tube within the array. A housing of device 1620 includes several openings including a cavity 1623 in which a user's nose is placed. As shown, a PCB 1622 and tube array 1621 is positioned opposite an exhaust 1624 located at the other side of the device. FIG. 16D shows another view of the device (now shown as device 1630) which shows relative positioning of the PCB and tube array with respect to the housing and openings. FIG. 16E shows another view of the device (e.g., as device 1630) whereby only the external housing and viewable elements are seen. As can be more clearly seen, the housing 1632 forms a cavity 1631 in which a user's nose may be positioned. Further, device 1630 includes a mounting surface 1633 which may be attached by one or more methods to an AR/VR headset, such that the device is positioned near the user's nose. It should be appreciated that elements shown in FIGS. 16A-16E (e.g., PCB elements, tube arrays, etc.) may be similar or the same items among the various figures, but may be substituted with other elements as described herein.

Figure 17A:
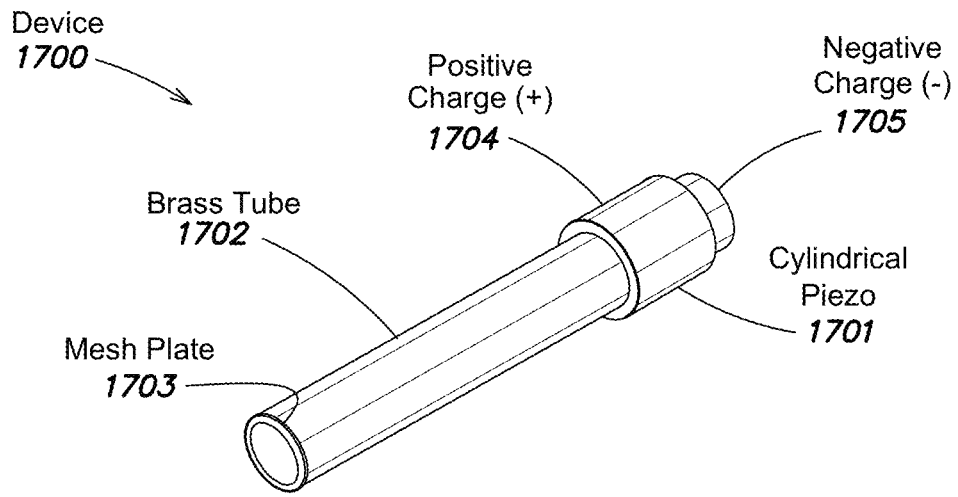
FIGS. 17A-17B show a device for generating atomized fluid according to some embodiments.
Figure 17B:
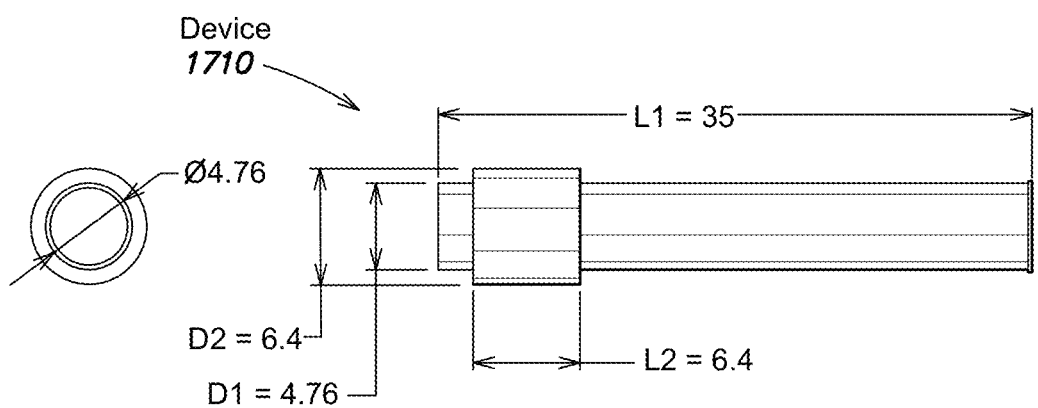

FIGS. 17A-17B show a device for generating atomized fluid according to some embodiments. In particular, FIG. 17A shows a round tube device 1700 similar in function to the device discussed above with respect to FIGS. 13A-13D. Device 1700 may include a tube 1702 having a length (L1) and diameter (D1). A piezoelectric sleeve is attached at an end of the cylindrical tube, the element having a length (L2) and diameter (D2). In some embodiments, the piezoelectric sleeve may be attached to the cylindrical tube via glue, epoxy, solder or other adhesive.

Similar to the rectangular embodiment, an aperture plate (e.g., mesh plate 1703) is attached to an end of the tube while a second end is open and is configured to receiving a fluid and supplying the fluid to the aperture plate through the tube. The piezoelectric element is connected to a circuit that generates an electrical signal at a frequency that is equal to the resonance frequency of tube and in an amplitude that is sufficient to produce a flow of atomized droplets. The electrical signal may be, in some embodiments, an alternating signal that is applied to contacts of the piezoelectric element (e.g., via positive charge 1704 being applied to the piezo layer and a negative charge 1705 being applied to the tube).

In one embodiment, the tube is made of brass and has a diameter of 4.76 mm, and a length of 35 mm, with a resonant frequency in a range of substantially 100-300 KHz. The piezo element may have a diameter of 6.4 mm and length of 6.4 mm. It should be appreciated however, that other dimensions, configurations and resonant frequencies may be used. For example, the range of the frequency that a particular device may function can vary from a relatively low frequency (e.g., 20 kHz) to a relatively high value (e.g., 1 GHz). Using the example circular tube devices described above, the resonant frequency may be determined to be in a range of 100-300 KHz. Generally speaking, if the size of the tube is decreased, the frequency increases, but it should be appreciated that the resonant frequency depends on a number of factors and can be determined heuristically from testing the device.

In some embodiments, the piezo element and tube form a unimorph device including an active layer (e.g., the piezo element) and an inactive layer (e.g., the tube surface). In some conventional piezo elements, they may use a pinching/squeezing mechanism to deliver liquids, however, in some embodiments as disclosed herein, a medium (e.g., a liquid) is aerosolized via perpendicular acoustical waves induced by a piezo element. It should be appreciated that although certain shaped devices having certain dimensions are shown, other shaped elements having different dimensions may be used.

Figure 18:
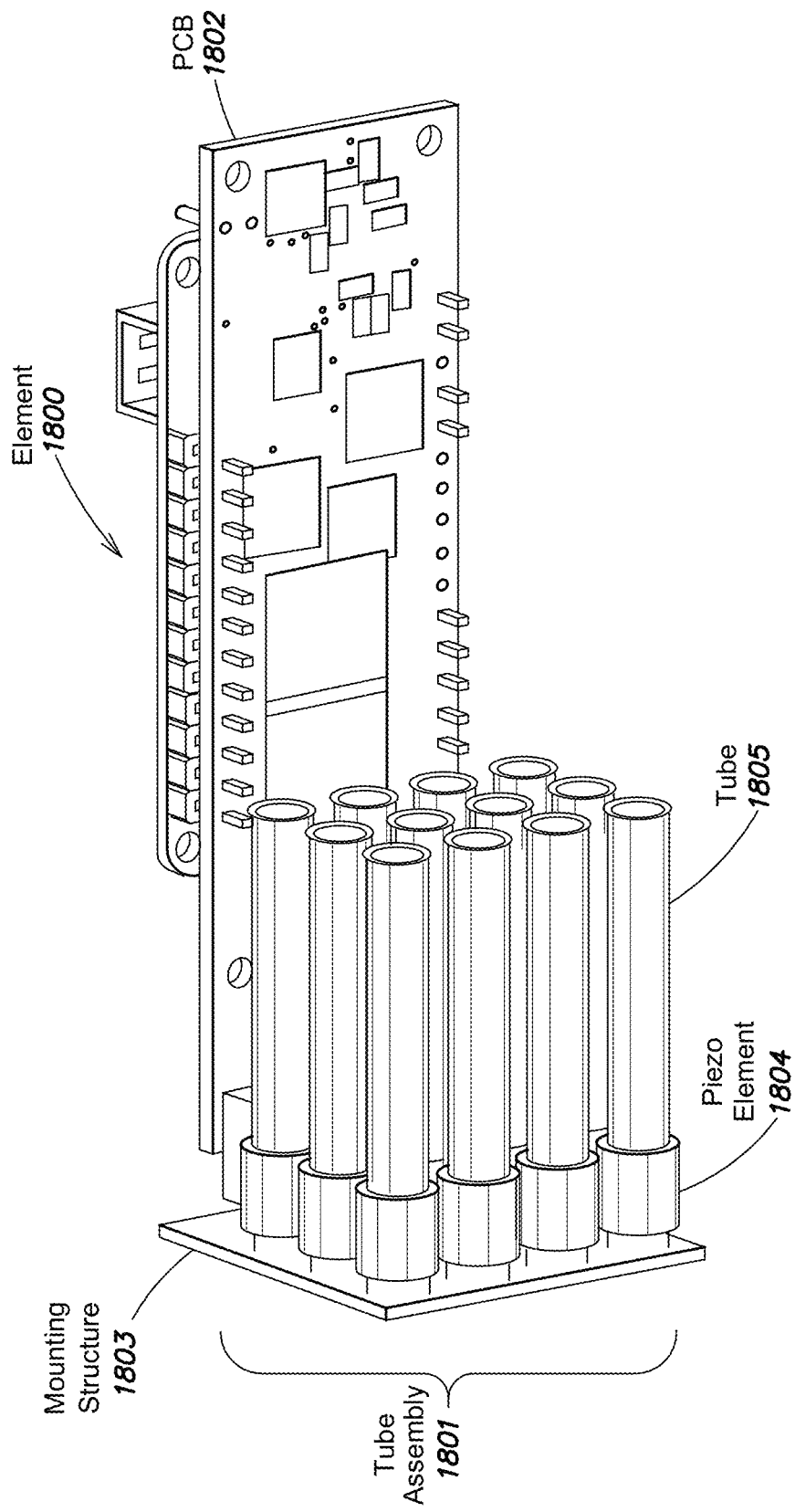
FIG. 18 shows a more detailed view of an element including a tube assembly according to some embodiments.

FIG. 18 shows a more detailed view of an element including a tube assembly according to some embodiments. In particular, FIG. 18 shows an element 1800 including a PCB 1802 having power and control circuitry that is used to selectively activate one or more piezo-based tubes within a tube assembly 1801. Each of the tubes (e.g., tube 1805) may be mounted on a mounting structure 1803. In some embodiments, the tubes are mounted to isolate them vibrationally from other tube elements. In some cases, spacers or other elements may isolate the tube elements. In some embodiments, piezo elements of each tube (e.g. piezo element 1804) are positionally separated by adjacent tubes yet are mounted by a common electrical connection (e.g., via a separate PCB). In some cases, there may be isolation elements that isolate each tube from the mounting structure.

Cartridge-Based System

In some embodiments as described herein, a convenient system with replacement hardware is provided for rendering scents within a computing environment. In some implementations, a scent cartridge unit is provided that is replaceable within a scent-rendering hardware unit that is computer-controlled to render one or more scents to be experienced by a user. The scent-rendering hardware unit includes one or more aerosol generators that are adapted to release individual scents.

As discussed, the cartridge may include a replaceable scent cartridge portion and a cartridge portion that contains scent-rendering hardware (e.g., such as controller circuitry, aerosol generators, etc.). The replaceable scent cartridge may be attached to the scent-rendering hardware unit using one or more coupling elements. The scent-rendering hardware unit may in turn, be mounted within an overall unit for rendering scents, such as an AR/VR system or other type of scent-rendering system.

The scent-rendering hardware unit may include multiple aerosol generator elements positioned in an array. In some embodiments, the scent-rendering hardware unit may include the aerosol generator units and associated circuitry along with a controller that is adapted to receive signals from one or more other systems (e.g., a gaming system, AR/VR system, etc.) to render scent to a user. In some embodiments, the replaceable scent cartridge may include individual scent media (e.g., liquids) located within small cavities within the cartridge. In various implementations, the replaceable cartridge may "plug" into the scent-rendering hardware unit which includes the aerosol generator units which atomizes the various scent media. In some embodiments, the scent-rendering hardware unit may include any necessary driver circuitry that drives the aerosol generator units. In some alternative embodiments, the aerosol generators may form part of the replaceable scent cartridge portion.

Figure 19A:
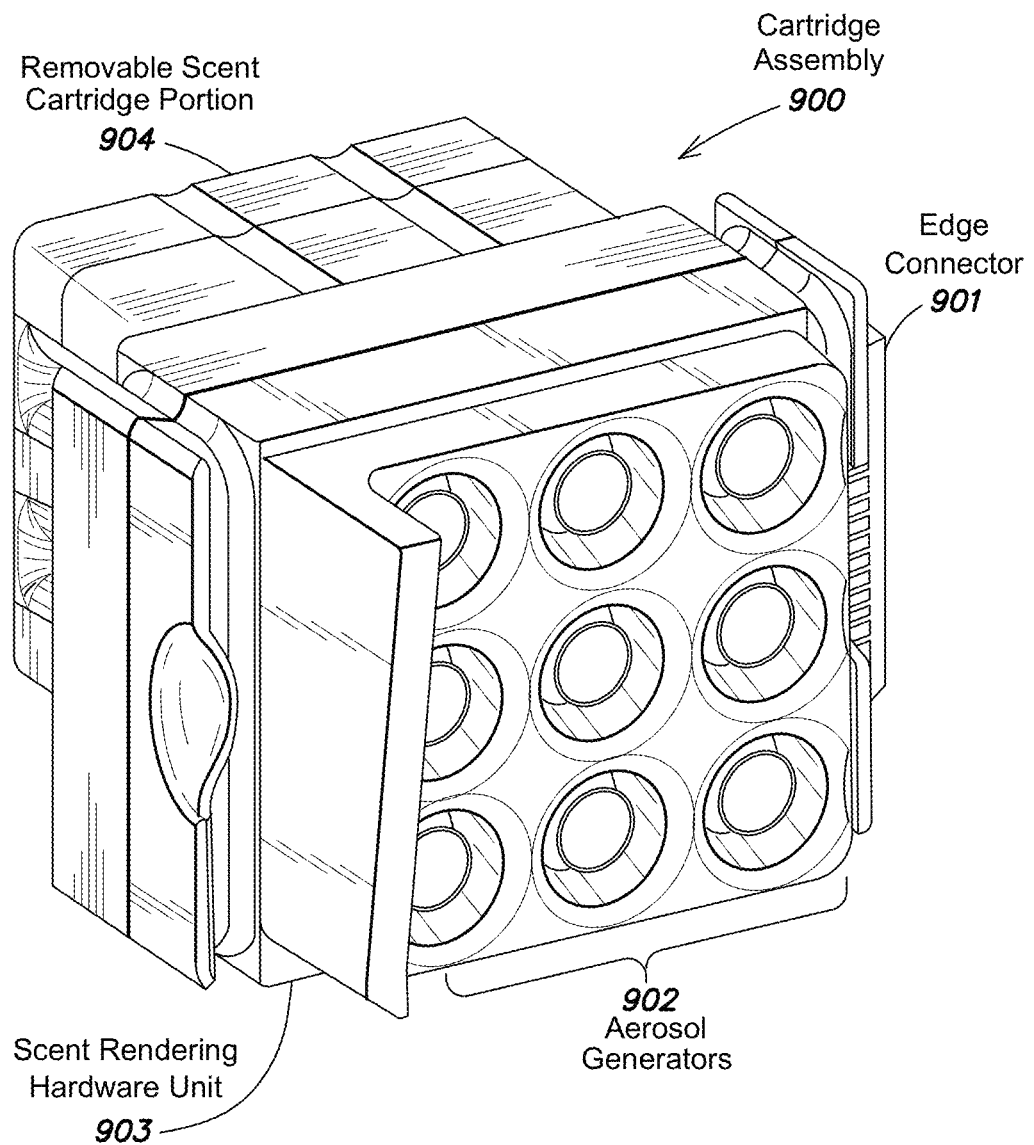

FIGS. 19A-19F show various embodiments of a cartridge-based system for rendering scent information. In FIG. 19A, a cartridge assembly 900 includes several portions, including a scent rendering hardware unit (e.g., unit 903) and a removeable scent cartridge portion (e.g., portion 904). In some embodiments, the scent rendering hardware unit includes elements for generating scent including, but not limited to aerosol generators (e.g., aerosol generators 902), any associated driver circuitry, and any connection elements to the overall system (e.g., edge connector 901).

The cartridge portions themselves may be constructed using polypropylene plastic (PP) or other suitable material.

It is noted that some of the surface materials used that are in contact with the scented liquid or other media may be selected to increase hydrophobicity to permit the liquid (or other media) to more freely flow within the cartridge. Further, one or more surfaces may have coatings to increase hydrophobicity (and increase oleophilic qualities of the surface). The cartridge portions may include additional elements such as nozzle guards, shields, and/or coupling mechanisms to effectively integrate within a scent rendering assembly (e.g., please see FIG. 19B). As discussed above, the cartridge may also include one or more elements (e.g., microfluidics elements to facilitate the delivery of the scented liquid or other media.

The cartridge portions may also include one or more coupling elements such as latches and/or types of connectors (e.g., strong magnets) that tightly couple the scent rendering hardware unit (e.g., unit 903) and a removeable scent cartridge portion (e.g., portion 904) when inserted. Various portions of the cartridge may form a seal or provide sealing forces to contain the cartridge media. Because the removeable scent cartridge portion may be provided as a replacement item and may need to exist separate from the scent rendering hardware unit, a temporary cover (e.g., a molded plastic cap) may be provided (not shown) that provides a seal to the ends of the tubes and wicks of the removeable scent cartridge portion to reduce evaporation and ensure longevity in storage. In some embodiments, the molded cap includes open cell foam dots that create a seal near the tip of each wick/tube of the removeable scent cartridge portion. Further, when the removeable scent cartridge portion is inserted within the scent rendering hardware unit, there may be additional seals that reduce the amount of evaporation and decrease the chance of media flowing between the aerosol generators and out of the cartridge assembly. For instance, a seal (e.g., using an open cell foam gasket) positioned near the distal end of the brass tubes to create a small sealed volume of air.

Figure 19B:
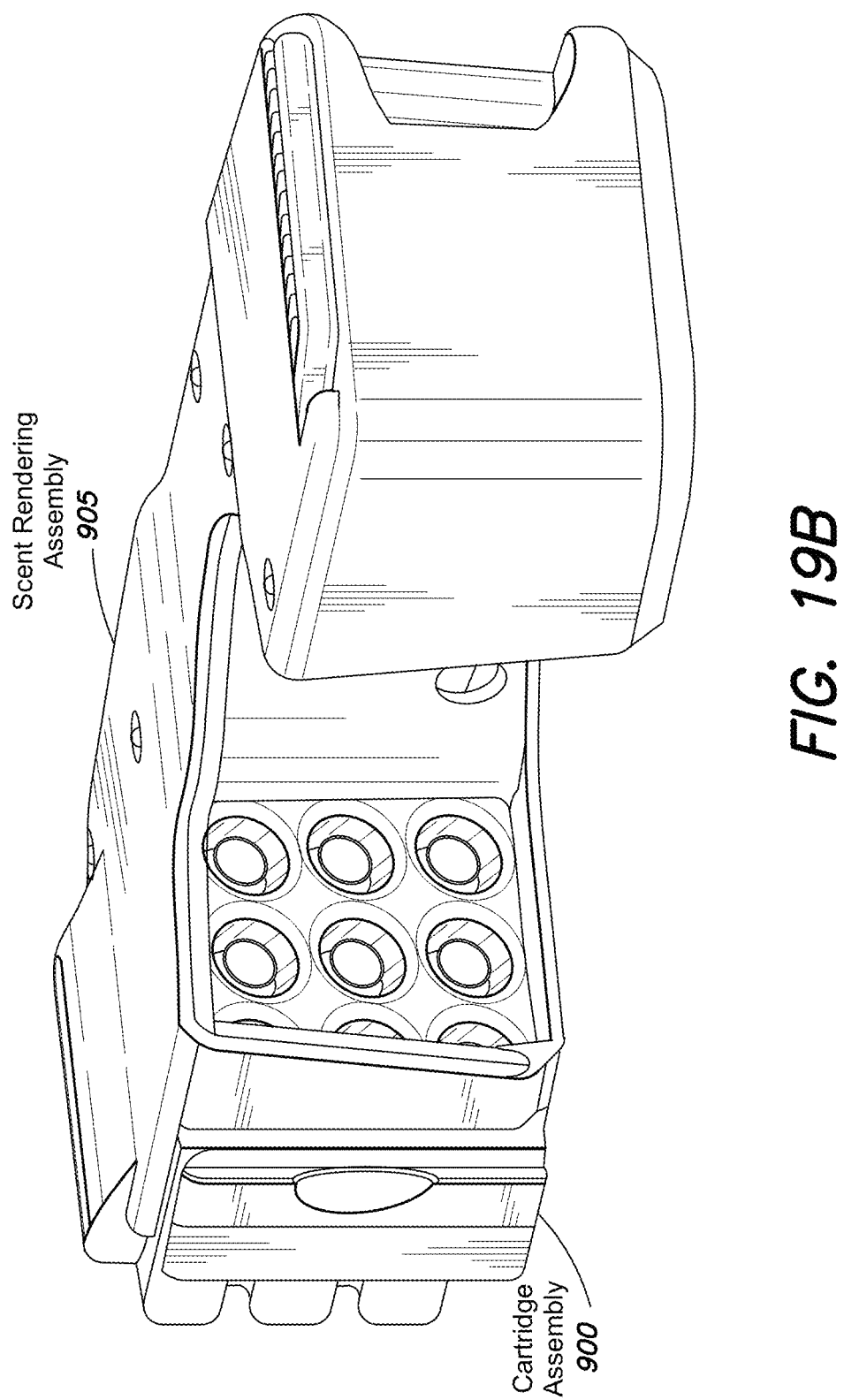

FIG. 19B shows an example implementation where the cartridge assembly is inserted within a scent rendering assembly (e.g., assembly 905). As shown the cartridge assembly is positioned such that the outlets of the aerosol generators are directed to an area which can be positioned near a user's nose. The scent-rendering assembly can be coupled to a bottom portion of an AR/VR headset via one or more attachments. In some embodiments, the removeable scent cartridge portion is accessed external to assembly 905, where it can be easily replaced.

Figure 19C:
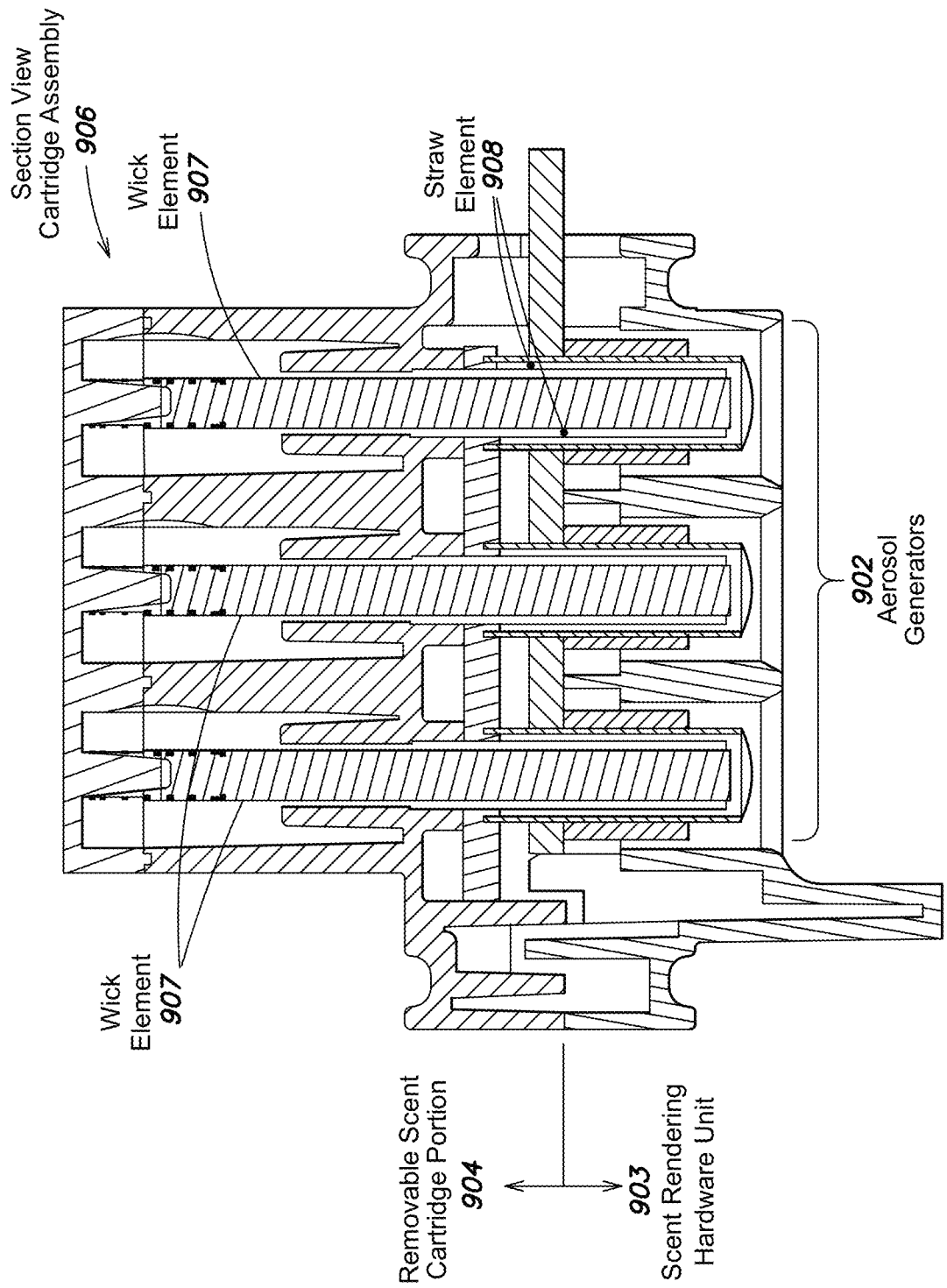

FIG. 19C shows a sectional view of cartridge assembly 900 (element 906). The cross-sectional view shows a slice of three chambers at their mid-sections, which exposes dividing of the removable scent cartridge portion 904 and scent rendering hardware unit 903. The removable scent cartridge portion includes multiple chambers (one for each aerosol generator) that holds the different scented media. A straw element extends through an aerosol generator of the scent-rendering hardware unit and contacts the plate of the particular aerosol generator.

As shown, the removable scent cartridge portion 904 includes multiple wick elements (one for each aerosol generator) which each extend through respective straw elements (e.g., elements 908) of the removable scent cartridge portion 904 to insert within the aerosol generators 902. Note that there may be an isolation gap between an exterior surface of the straw element and the interior surface of the aerosol generator into which the straw element inserts to permit, for example, the piezoelectric element to vibrate.

As discussed above, wicking elements may be used to transfer liquid or other types of scented media from chambers located in the removable scent cartridge portion 904 to the aerosol generators 902 of the scent rendering hardware unit. As an alternative or in addition to wick elements, the system may use one or more other component elements to provide liquid movement. For example, the system may use one or more microfluidics elements (e.g., micropumps, microvalves, capillary flow modifying elements, etc.) to transport, mix, separate, or otherwise process the scented liquids(s).

FIG. 19D shows cartridge assembly 900 with an encasing front portion (e.g., a plastic cover) removed to show the aerosol generators 919 and attached PCB board assembly 918. The plastic cover (not shown) may include one or more seals that are coupled to the distal ends of the aerosol generators 919 tubes to provide additional sealing and protection of the aerosol generator elements.

Figure 19E:
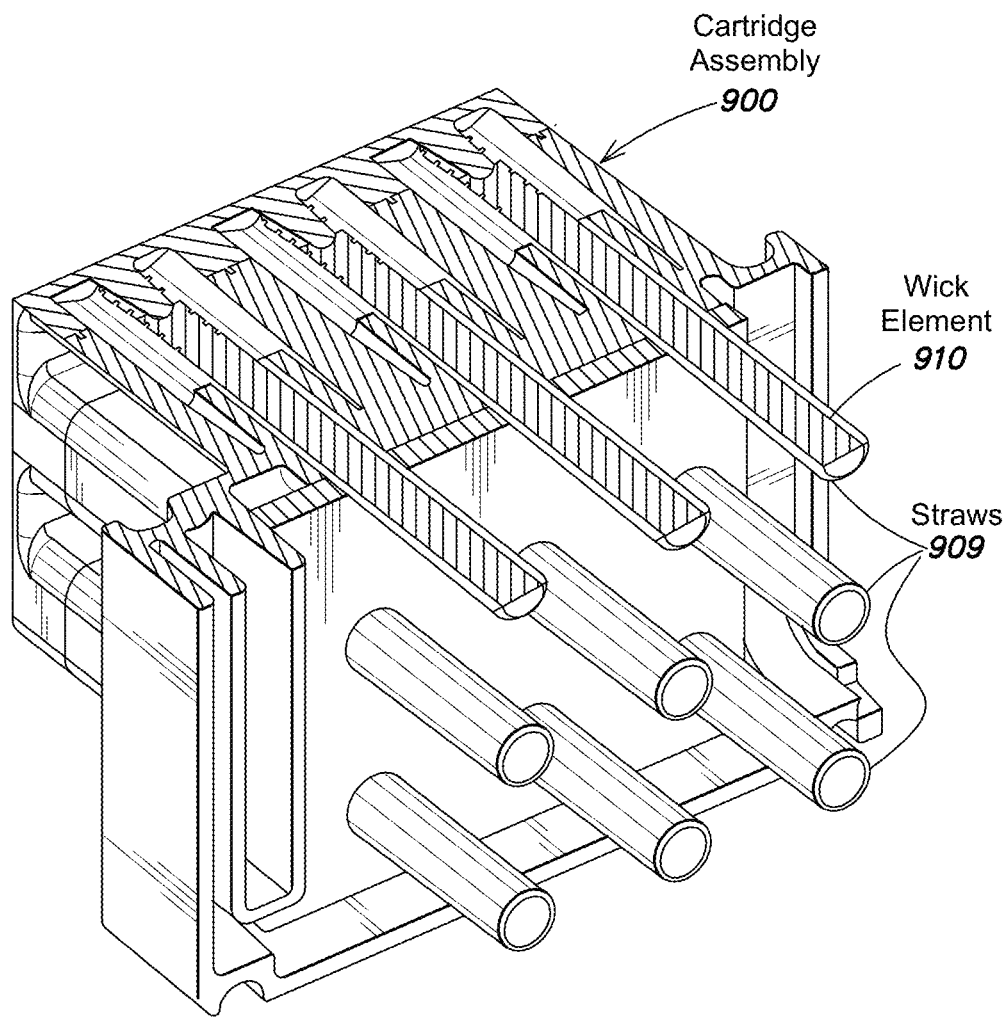

FIG. 19E shows cartridge assembly 900 without the scent rendering hardware unit 903 and its aerosol generators, exposing the straws (e.g., 909) and wick (e.g., 910) elements. As can be seen, the straw elements extend outward and are insertable in the tubes of the aerosol generators. A cutaway view of wick element 910 shows the straw element positioned within its respective straw element.

Figure 19F:
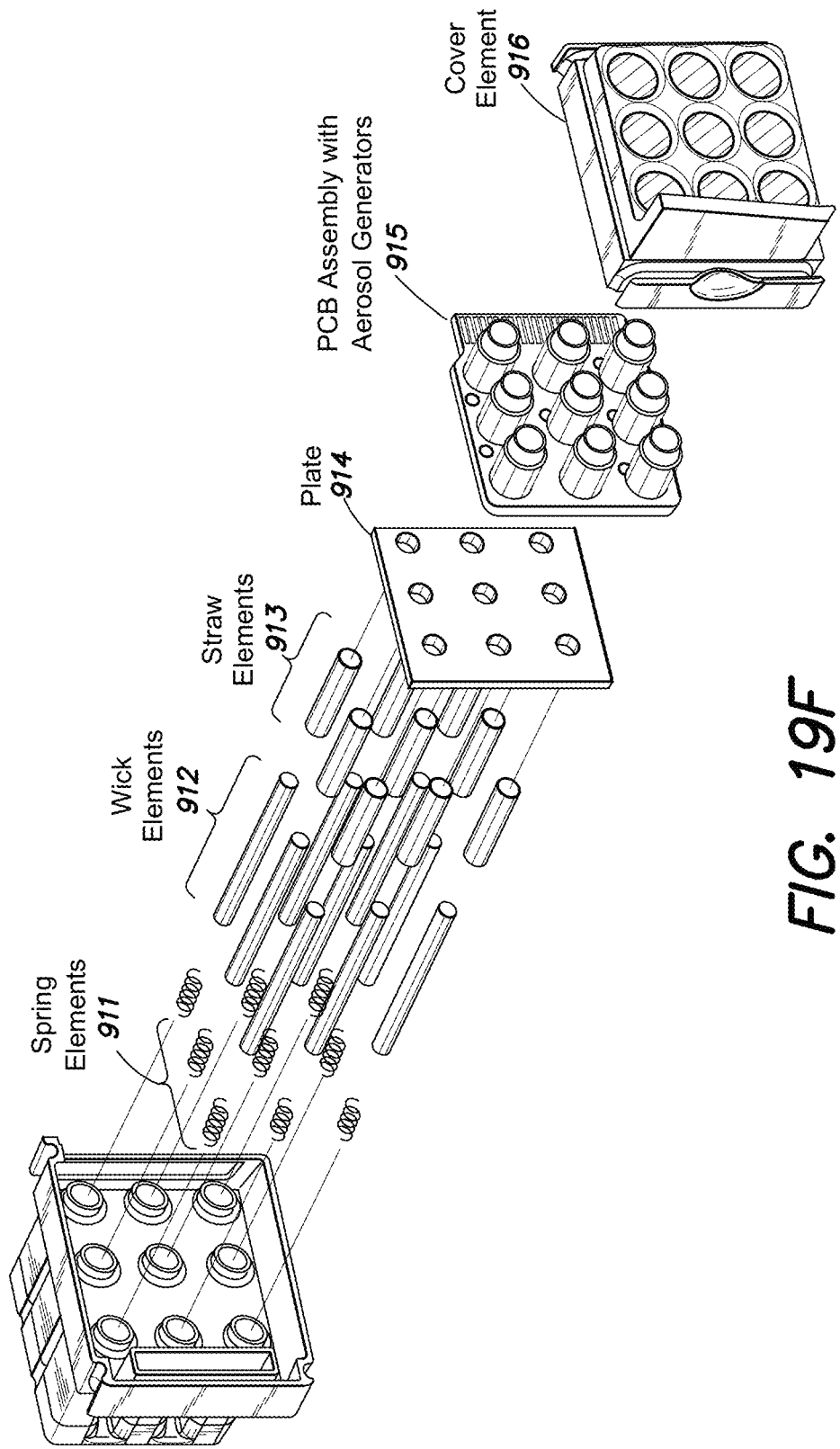

FIG. 19F shows an expanded view of the elements within the cartridge assembly 900. Notably, the cartridge assembly may include one or more elements that cause wick elements (e.g., wick elements 912) to contact a plate within the aerosol generators. Such elements could be springs (e.g., spring elements 911) but it should be appreciated that force may be applied using other methods (e.g., by the cartridge housing itself). The wick elements 912 extend through respective straw elements that are extended through a plate 914 into tubes of the aerosol generators. The aerosol generators are coupled to a PCB assembly (e.g., assembly 915). The assembly may include a cover element 916 which provides additional protection for the aerosol generators, and sealing of the components. It can be constructed of a hard plastic or other material. As can be appreciated, the cartridge may include any number of chambers and aerosol generators, and the system is not limited to any particular number. Below are described some example aspects of the system which can be used alone or combined with other embodiments.

Other Applications

Although such devices may be used in gaming and entertainment applications, it should also be appreciated that such a system may be useful in a number of different applications outside the gaming/entertainment area such as, for example:

Cognitive behavioral therapy (cognitive behavioral therapists use a number of techniques to help their patients work through traumatic experiences including exposure therapy and virtual reality. It is appreciated that conditions such as PTSD from war and sexual trauma are the hardest to overcome for one reason: smell, these experiences are hardwired into our brains. By integrating unique, curated aromas into the therapy with VR, thousands of people may be helped to live normal lives and have normal relationships.

Remote surgery. It is appreciated that people's sense of smell works more quickly and efficiently than all of our other senses combined. VR has the unique ability to allow surgeons to perform complicated surgeries remotely but still only effectively offers 2D sense of objects during complex procedures. By augmenting the surgeon's sense of critical areas with scent, the chance of error may be decreased without the need for the surgeon to break visual plane)

Sight impaired. For the visually impaired to participate in VR or AR, various systems must take advantage senses other than eyesight.

Forensics. Witnesses identifying the perpetrator is dangerously inaccurate and subject to implicit bias. Because of the direct link between scent, memory and emotion, VR may be coupled with scent creating a stronger, impartial, more just method of suspect identification, crime scene analysis and jury trials).

Therapeutic uses. Office, team, family, and relationship productivity goes up dramatically when people feel calm, rested and refreshed. For example, spending 10 minutes in scent enhanced, augmented reality can offer the same benefits as meditation, sleep or an hour of mindfulness.

Sports medicine. Training in VR kick starts psychosomatic response (i.e., nothing can create a "Pavlovian response" more quickly and powerfully than scent training. When an athlete is training for an event—like the Tour de France for example—in VR, aromatic stimuli may be created that increase or decrease heart rate, testosterone, or even pain/pleasure response that will be recreated during actual competition.

Piloting. As aeronautics and combat become more technologically advanced, any opportunity to make controls and feedback more intuitive to the pilot is paramount. It is appreciated that very second the pilot has to pay attention to a gauge or otherwise take his eye off more important visual cues can have catastrophic events. Furthermore, in high stress combat situations quick decision making without hesitation is key. Because smell stimulates the limbic (fight or flight) portion of the brain before being processed by the pre-frontal cortex, it is appreciated that VR training simulations utilizing olfactory cues can increase response time, preserve focus and decrease stress responses in real life situations.

Transposing senses and environmental conditions. For example, information of the environment such as temperature, humidity, radiation, unscented poisonous gas. (rov exploration in environments that are dangerous or toxic to humans rely too heavily on sight and crude robotics. By utilizing a VR/AR interface with a detection capability of scent that can be translated and communicated to an OVR system, the capability may be provided to explore the deep sea, radioactive sites, caves, and the like. In particular, human operators can receive and interpret data in real time in a much more meaningful way than ever before.

Space applications. Astronauts often need to be able to sense physical phenomena on the edge of perception, e.g., gamma rays, x rays, oxygen and carbon dioxide levels, and an OVR system may be used to accomplish experiencing these environments.

In some embodiments, an atomizer is provided for dispensing liquids into the air. In some implementations, a device is provided for generating atomized fluid specifically, but not exclusively, for production of small droplets of scented oil and other fluid-based fragrances, among other types of liquids. In some embodiments, the device comprises a tube having a proximal opening and a distal opening, wherein media inside the tube is forced out of the proximal opening via an aperture plate, examples of which are shown in FIGS. 13A-13D and 17A-17B. Such tubes may have any shape and size, such as rectangular or cylindrical tubes.

In some embodiments, the tube further includes at least one piezoelectric plate that is attached to a face of the tube. The device further includes an aperture plate that is attached to the proximal end of the tube whereas the distal end of the tube is connected to a fluid supply source for supplying fluid through the tube to aperture plate at the proximal end of the tube. In some embodiments, the aperture plate includes a plurality of conical apertures that extend through the thickness of the plate.

In some embodiments, the device comprises a tube having a proximal opening and a distal opening, wherein fluid enters the distal end and is forced out of the proximal opening via an aperture plate. In some embodiments, fluid may be existing within the tube and/or added via the distal end, such as by a mechanism to add fluid as the device operates and forces the fluid out. In some embodiments, the device is provided with the fluid located within the tube.

The device further includes a signal generator circuit capable of producing an electrical signal at a selected frequency and voltage. When the frequency generator is connected to the piezo plate, cyclical stress waves are generated by the piezo plate which subsequently propagates along the length of the tube and produces oscillation which vibrates the aperture plate and generates a flow of atomized liquid through the apertures. In some embodiments, it is desirable that at least one surface of the tube has sufficient surface area and enables attachment of the piezo substrate. In some embodiments, the tube may be rectangular in shape, and a surface of the piezo substrate may be affixed to a substantial portion of a surface of the tube. In some embodiments, the piezo element is positioned more closely to distal end, allowing the stress waves to travel more significantly to the proximal opening.

In some embodiments, a single piezo attached to the tube generates longitudinal oscillation within the tube. In some embodiments, the tube does not bend due to the tube shape structure having a very high bending stiffness due to high moment of inertia of the tube's cross sectional shape. However, vibration is produced within the tube as the piezo may vibrate with a resonant frequency of the tube, and the cyclical stress waves force the liquid through the apertures.

In some embodiments, a plurality of devices may be placed in a linear array. In such an arrangement, it may be desirable that one side of the tube will be narrow such that multiplicity of devices can be stacked together with a minimum space.

In some embodiments, the induced frequency produced by the piezo element is equal to the natural frequency of the rectangular tube in a longitudinal mode or bending mode.

In some embodiments, the tube is a rectangular tube having two wide faces such that the area of at least one of the faces is sufficiently wide to attach at least one piezoelectric element that is capable of generating a sufficient amplitude.

In some embodiments, the tube has trapezoidal cross-sectional shape and having at least one face that is sufficient to attach at least one piezoelectric element that is capable of generating a large amplitude.

In one embodiment the tube is circular in cross-sectional shape and having one face that is sufficient to attach at least one piezoelectric element that is capable of generate large amplitude.

In one specific embodiment, the width of the tube is between 0.05 mm to 0.1 mm and the length between 1 mm and 45 mm. In some embodiments, it is appreciated that a small device may be preferred for some applications, yet the size may be optimized so as to not require an excessively large resonant frequency. In some embodiments, the aperture plate is secured to the end of the tube via solder or glue and covers the entirety of the end of the tube. In some techniques, the aperture plate is circular and bent before connecting to edge of the tube. Additionally, the aperture plates may be flat or domed with the dome shaped outward from the end of the tube.

In some other applications, the aperture plate is sized to fit perfectly on the end of the tube. In some implementations, aperture sizes may be less than approximately 10 µm. For instance, apertures of approximately 5 µm range (+/−2 µm) may work for some applications. Generally, smaller aperture sizes are preferred, but the aperture sizes may be optimized to reduce clogging and the amount of force necessary to generate atomized fluid.

Example Implementations

One example use of such a device according to various embodiments includes aerosol generation of scented liquids (such as for an AR/VR application described in an example application), but it can also be for turning any liquid (e.g., aqueous and non-aqueous) into a mist.

In particular, the device is used to atomize scented material, i.e., the ability to turn scented liquids into mist using vibration and micro-pores to allow the scent permeate in the air in specific quantities.

In other examples, the device may be used to atomize media such as liquid forms of *cannabis* into aerosol for inhalation: For instance, liquid forms of *cannabis* or cbd oils, waters or other aqueous solutions may be atomized and inhaled by users. Other media that may be used could include emulsions, solutions, mixtures, and inclusions. In such a case, the generator device may be part of a larger delivery mechanism (e.g., an e-cigarette, vaporizer, or other device) that allows users to inhale atomized liquids or other media types.

In some other applications, the device may be used for dispersing medical liquids (e.g., dispersing certain medicines in an atomized form for inhalation using conventional VMT technology. For instance, VMT devices used in nebulizers could be adapted using some of the embodiments described herein for that purpose.

Some other applications include:
gel to liquid conversion: certain theoretic gels have attributes where vibration turns them from a gel into a liquid which would allow for atomization through the device. This could be used primarily to do gel coatings as after vibration, the liquid would coalesce back into a gel.
volatile liquid atomization—alcohol, ethanol, gasoline, Benzine: For instance, it may be beneficial to able to atomize various less-common liquids for reasons like combustion engines.
water humidification In some embodiments, the size specification for the device may be relatively small, especially in applications where multiple devices may be used in parallel, such as within a larger device. Other applications (such as an e-cigarette application), the permitted dimension and/or may be limited to a relatively small form factor. Other applications may use a larger form factor, such as a large mist "cannon" that could be used to vaporize large amounts of water or scent or used as part of an engine.

One implementation includes a tube having a rectangular or square in shape. In some conventional piezo elements, they may use a pinching/squeezing mechanism to deliver liquids, however, in some embodiments as disclosed herein, a medium (e.g., a liquid) is aerosolized is via perpendicular acoustical waves induced by a piezo element.

In some implementations, there are a few ways that the medium can come into contact with the plate.
Free in housing: the liquid is just free in the tube and capped at the end opposite the aperture plate end to seal inside. The vibration pattern forces the liquid in contact with the plate.
Wick: A wick is placed in the tube and capped in with the liquid to force the correct capillary action to move the liquid to plate in conjunction with the vibration. In some embodiments, the wick may be shaped to fill the area within the tube (e.g., a rectangular, tubular, or square shape). In some implementations, the wick element may be a replaceable item, and may be accessible to be replaced. The wick may also be part of or coupled to a reservoir that holds liquid to be dispersed. The wick may be, in some embodiments, bidirectional or unidirectional wicking material made out of, for example, natural fibers and/or synthetic fibers including cotton, polyethylene, nylon, metal, graphene, among others.
Cartridge: A cartridge of custom design is inserted into the back to the tube with a connection point to the tube and plate. The cartridge may, or may not, use a wick or material that has a wicking property.

It should be appreciated that there are other applications of this technology and the invention is not limited to the examples provided herein. For example, some embodiments may be used in general entertainment, which could be movies or other experiences. Additionally, some embodiments may be applied to areas such as travel, business, education/training, telepresence, and meditation.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A cartridge comprising:
a plurality of chambers, each having a media delivery channel, each media channel being configured to be coupled to a respective aerosol generator within a scent-rendering hardware unit; and
a plurality of scented media, each one assigned to a respective one of the plurality of chambers, wherein each media channel includes a straw element including a wick element that is configured to deliver scented media to the respective aerosol generator within a scent-rendering hardware unit.

2. The cartridge according to claim 1, further comprising a coupling that attaches the cartridge to the scent-rendering hardware unit, wherein the cartridge is a replaceable item and is adapted to be removable from the scent-rendering hardware unit.

3. The cartridge according to claim 1, wherein each of the media channels includes a respective capillary mechanism per respective chamber to its respective aerosol generator.

4. The cartridge according to claim 3, further comprising a component that provides a force to the capillary mechanism that maintains contact between the capillary mechanism and a portion of its respective aerosol generator.

5. The cartridge according to claim 3, wherein the component that provides force to the wick element includes a spring.

6. The cartridge according to claim 4, wherein the component that provides force to the capillary mechanism includes at least one of a group comprising:
- microfluidic forces;
- a physical component coupled to a housing of the cartridge; and
- a spring.

7. The cartridge according to claim 2, wherein the wick element is in contact with a plate of the aerosol generator, and liquid is transferred from the chamber to the plate of the aerosol generator by capillary action.

8. The cartridge according to claim 1, wherein the aerosol generator within a scent-rendering hardware unit includes at least one piezoelectric element.

9. The cartridge according to claim 1, further comprising a sealing mechanism that creates a seal between an interior surface of each aerosol generator and an exterior surface of a respective straw element.

10. The cartridge according to claim to claim 1, wherein the respective aerosol generator is a replaceable item and is adapted to be removable from the scent-rendering hardware unit.

11. A system incorporating the cartridge of claim 1.

12. A cartridge comprising:
- a plurality of chambers, each having a media delivery channel, each media channel being configured to be coupled to a respective aerosol generator within a scent-rendering hardware unit;
- a plurality of scented media, each one assigned to a respective one of the plurality of chambers; and
- a temporary cap element that is configured to be removed prior to coupling the cartridge to the scent-rendering hardware unit.

13. The cartridge according to claim 12, wherein the temporary cap element includes one or more seals of a plurality of the media delivery channels.

14. The cartridge according to claim 13, wherein the temporary cap element includes open cell foam elements that seal a tip of a wick/tube element of the cartridge.

15. A cartridge comprising:
- a plurality of chambers, each having a media delivery channel, each media channel being configured to be coupled to a respective aerosol generator within a scent-rendering hardware unit; and
- a plurality of scented media, each one assigned to a respective one of the plurality of chambers, wherein the respective aerosol generator is combined with the cartridge and is coupled together in order to be used as a single removable and replaceable unit.

* * * * *